US012064202B1

(12) United States Patent
Grotenhuis et al.

(10) Patent No.: US 12,064,202 B1
(45) Date of Patent: Aug. 20, 2024

(54) SYSTEMS AND METHODS FOR ALLOWING REMOTE ROBOTIC SURGERY

(71) Applicant: Sovato Health, Inc., Huntington Beach, CA (US)

(72) Inventors: Tyler Grotenhuis, Santa Barbara, CA (US); John Lawrence, Santa Ynez, CA (US)

(73) Assignee: Sovato Health, Inc., Huntington Beach, CA (US)

( * ) Notice: Subject to any disclaimer, the term of this patent is extended or adjusted under 35 U.S.C. 154(b) by 0 days.

(21) Appl. No.: 18/541,688

(22) Filed: Dec. 15, 2023

Related U.S. Application Data

(60) Provisional application No. 63/599,285, filed on Nov. 15, 2023, provisional application No. 63/599,232, filed on Nov. 15, 2023.

(51) Int. Cl.
| | |
|---|---|
| *A61B 34/37* | (2016.01) |
| *G16H 40/20* | (2018.01) |
| *G16H 40/40* | (2018.01) |
| *G16H 40/67* | (2018.01) |
| *G16H 80/00* | (2018.01) |

(52) U.S. Cl.
CPC ............. *A61B 34/37* (2016.02); *G16H 40/20* (2018.01); *G16H 40/40* (2018.01); *G16H 40/67* (2018.01); *G16H 80/00* (2018.01)

(58) Field of Classification Search
CPC ........ A61B 34/37; G16H 40/20; G16H 40/40; G16H 40/67; G16H 80/00
See application file for complete search history.

(56) References Cited

U.S. PATENT DOCUMENTS

| 7,158,859 B2 | 1/2007 | Wang et al. |
| 7,158,860 B2 | 1/2007 | Wang et al. |
| 7,161,322 B2 | 1/2007 | Wang et al. |
| 7,171,286 B2 | 1/2007 | Wang et al. |
| 7,222,000 B2 | 5/2007 | Wang et al. |
| 7,262,573 B2 | 8/2007 | Wang et al. |
| 7,761,185 B2 | 7/2010 | Wang et al. |
| 7,769,492 B2 | 8/2010 | Wang et al. |
| 8,116,910 B2 | 2/2012 | Walters et al. |
| 9,610,685 B2 | 4/2017 | Wang et al. |
| 9,616,576 B2 | 4/2017 | Roe et al. |

(Continued)

OTHER PUBLICATIONS

Ghodoussi et al., "Robotic Surgery—The Transatlantic Case", Proceedings of the 2002 IEEE International Conference on Robotics & Automation, Washington, DC, May 2002, pp. 1882-1888.

(Continued)

*Primary Examiner* — Basil T. Jos
(74) *Attorney, Agent, or Firm* — Knobbe Martens Olson & Bear, LLP

(57) ABSTRACT

Approaches for granting control of robotic surgery systems located at patient-side locations are disclosed. Prior to granting control, disclosed approaches verify one or more of: compatibility of a surgeon console with a patient-side robotic surgery system, that a two-way audio and/or video communication between the patient side and surgeon side has been established, and that at least one network connection between the surgeon console and the patient-side robotic surgery system satisfies one or more network condition criteria. Disclosed approaches safeguard patient safety.

20 Claims, 14 Drawing Sheets

(56) References Cited

U.S. PATENT DOCUMENTS

| | | |
|---|---|---|
| 10,241,507 B2 | 3/2019 | Wang et al. |
| 10,259,119 B2 | 4/2019 | Wang et al. |
| 10,343,283 B2 | 7/2019 | Pinter |
| 10,493,631 B2 | 12/2019 | Wang et al. |
| 10,764,339 B2 | 9/2020 | Pinter et al. |
| 10,769,739 B2 | 9/2020 | Southard et al. |
| 10,808,882 B2 | 10/2020 | Wang et al. |
| 10,871,889 B2 | 12/2020 | Ballantyne et al. |
| 10,875,183 B2 | 12/2020 | Herzog et al. |
| 10,878,960 B2 | 12/2020 | Wang et al. |
| 10,882,180 B2 | 1/2021 | Wright et al. |
| 10,882,190 B2 | 1/2021 | Wang et al. |
| 10,887,545 B2 | 1/2021 | Stuart et al. |
| 10,889,000 B2 | 1/2021 | Wang et al. |
| 10,911,715 B2 | 2/2021 | Wang et al. |
| 10,969,766 B2 | 4/2021 | Wang et al. |
| 10,984,916 B2 | 4/2021 | Celmins et al. |
| 11,205,510 B2 | 12/2021 | Ross et al. |
| 11,389,962 B2 | 7/2022 | Pinter et al. |
| 11,468,983 B2 | 10/2022 | Wang et al. |
| 11,482,326 B2 | 10/2022 | Kahn |
| 11,628,571 B2 | 4/2023 | Pinter et al. |
| 11,636,944 B2 | 4/2023 | Hanrahan et al. |
| 2003/0071893 A1 | 4/2003 | Miller et al. |
| 2007/0130457 A1 | 6/2007 | Kamat |
| 2009/0326979 A1 | 12/2009 | Ryan |
| 2010/0076600 A1 | 3/2010 | Cross |
| 2011/0187875 A1 | 8/2011 | Sanchez et al. |
| 2011/0190930 A1 | 8/2011 | Hanrahan et al. |
| 2011/0213210 A1 | 9/2011 | Temby |
| 2012/0191464 A1 | 7/2012 | Stuart et al. |
| 2013/0293373 A1 | 11/2013 | Gegner |
| 2015/0092037 A1 | 4/2015 | Wang et al. |
| 2016/0368146 A1 | 12/2016 | Mangaser et al. |
| 2017/0300654 A1 | 10/2017 | Stein |
| 2018/0250086 A1 | 9/2018 | Grubbs |
| 2018/0257233 A1 | 9/2018 | Wright et al. |
| 2018/0297210 A1 | 10/2018 | Peterson |
| 2018/0308565 A1 | 10/2018 | Pinter et al. |
| 2018/0322255 A1 | 11/2018 | Connell, II |
| 2019/0009360 A1 | 1/2019 | Aoki |
| 2019/0088364 A1 | 3/2019 | Wang et al. |
| 2019/0134818 A1 | 5/2019 | Mangaser et al. |
| 2019/0174322 A1 | 6/2019 | Deviprasad |
| 2019/0188992 A1 | 6/2019 | Bodurka |
| 2019/0326015 A1 | 10/2019 | Cannell |
| 2020/0066414 A1 | 2/2020 | Neff |
| 2020/0169856 A1 | 5/2020 | Yang |
| 2020/0197116 A1 | 6/2020 | Linebarger |
| 2020/0203000 A1 | 6/2020 | Neville |
| 2020/0222129 A1 | 7/2020 | Gomez |
| 2020/0237224 A1 | 7/2020 | Sanchez et al. |
| 2020/0360607 A1 | 11/2020 | Pfeiffer |
| 2021/0145526 A1 | 5/2021 | Robinson |
| 2021/0178597 A1 | 6/2021 | Pinter |
| 2021/0220064 A1 | 7/2021 | Kottenstette et al. |
| 2021/0298845 A1* | 9/2021 | Freiin von Kapri ... A61B 34/20 |
| 2022/0284994 A1 | 9/2022 | Ellis |
| 2022/0331054 A1 | 10/2022 | Kimball |
| 2023/0128665 A1 | 4/2023 | Kottenstette et al. |
| 2023/0364290 A1 | 11/2023 | Hamidi |

OTHER PUBLICATIONS

Gu et al., "Robotic surgery in China", The Innovation, Sep. 11, 2023, vol. 4, No. 5, in 2 pages.

Harvard Business Review, Can Remote Surgeries Digitally Transform Operating Rooms?, https://hbr.org/podcast/2023/09/can-remote-surgeries-digitally-transform-operating-rooms, Sep. 12, 2023, Downloaded Nov. 15, 2023, in 15 pages.

Karl Storz Endoscopy-America, "Agreements/contracts: Karl Storz, InTouch to develop new surgical mentoring tool", www.bioworld.com/articles/443201, Mar. 18, 2009, in 2 pages.

McCamant, SSII: Amid Aggressive MedTech M&A, Could Robotic Surgery Company Find Itself in Someone's Crosshairs?, https://www.moneyshow.com/articles/dailyguru-61587/ssii-amid-aggressive-medtech-m-and-a-could-the-robotic-surgery-company-find-itself-in-someones-crosshairs/#, Sep. 19, 2023, Downloaded from the Internet Nov. 15, 2023, in 2 pages.

Smith, Craig S., "AI Poised to Transform Video-Compression Landscape, Apple's WaveOne purchase heralds a new era in smart-streaming of AR and video", IEEE Spectrum, Apr. 12, 2023, in 6 pages.

Suermann, Amelia, "Data Reveal the Details about the Surgeon Workforce Shortage", The Bulletin, Feb. 4, 2022, in 5 pages.

Surgical Robotics Technology, "Monogram Orthopaedics Selects RTI Connext Anywhere as the Connectivity Software Solution", https://www.surgicalroboticstechnology.com/news/monogram-orthopaedics-selects-rti-connext-anywhere-as-the-connectivity-software-solution/, May 24, 2023, Downloaded Nov. 15, 2023, in 6 pages.

Teladoc Health, Teladoc HealthTM Care Location App ModuleTM User Guide, 2021, in 71 pages.

Teladoc Health, "Teladoc HealthTM Lite V2 & V3 Under Guide", 2021, in 65 pages.

Whooley, Sean, "FDA clears Insight Medbotics' MRI-compatible surgical robot", https://www.massdevice.com/fda-clears-insight-medbotics-mri-compatible-surgical-robot/, Sep. 13, 2023, Downloaded from the Internet Nov. 15, 2023, in 5 pages.

Whooley, Sean, "Quantum Surigcal wins CE mark to treat lung tumors with its surgical robot", https://www.massdevice.com/quantum-surgical-lung-tumors-surgical-robot/, Sep. 11, 2023, Downloaded from the Internet Nov. 15, 2023, in 4 pages.

Woods, Rae, "The State of the Healthcare Industry Heading Into 2024", Advisory Board, 2023, in 36 pages.

youtube.com, "InTouch Provider Access", https://www.youtube.com/watch?v=By9azc1zz3k, Downloaded Nov. 21, 2023, in 2 pages.

youtube.com, "Monogram Makes Orthopedic History! Fully Remote Robotic Surgical Demo", https://www.youtube.com/watch?v=j0OQk8mT-bs, Mar. 10, 2023, Downloaded Nov. 16, 2023, in 3 pages.

* cited by examiner

FIG. 9A

SOVATO

Welcome, Robert!

Case Details

Now
- 7:30a Dr. Fisher / Dr. Fowler — Ready for Surgeon — DOB 11/03/1972 — Age 50 — BRMC Main OR 3, Frontline Health
  CHRYSLER, Bert — Gastric Bypass — MRN 1314685 — Sex male — Bedside Surgeon: Greg Flower, MD — Circulating Nurse: Christy Cornings, RN — [View]

Up Next
- 7:45a Dr. Fisher / Dr. Willing — In Pre-op — DOB 02/19/1954 — Age 69 — HVMC Main OR 15, Appalachia Healthcare
  LAFLOUR, Martha — Inguinal Hernia — MRN 9367145 — Sex Female — Bedside Surgeon: Greg Willing, MD — Circulating Nurse: Anders Holmvick, RN — [View]

Today's Schedule — 1102

○ BRMC Main OR 3 ~15 Minutes late — 1104 ○ HVMC Main OR 15 On Time EDT — 1106 ⊘ GCH Main OR 4 On Time EDT
Frontline Health — PDT (-3:00) — Appalachia Healthcare — Frontline Health

| Time | BRMC Main OR 3 | HVMC Main OR 15 | GCH Main OR 4 |
|---|---|---|---|
| 7:00a | | Dr. Fisher / Dr. Willig — HOWE, Aiden — Cholecystectomy — 1116 — Closing | |
| 7:15a | | | XXXX, Xxxx — Dr. Toboggan — Procedure Start — Xxxxxx Xxxx |
| 7:30a | Dr. Fisher / Dr. Fowler — CHRYSLER, Bert — Ready for Surgeon — Gastric Bypass — 1108 | | |
| 7:45a | | Dr. Fisher / Dr. Willing — LAFLOUR, Martha — Inguinal Hernia — 1117 — In Pre-op | |
| 8:00a | | | XXXX, Xxxx — Dr. Toboggan — In Pre-op — Xxxxxx Xxxx |
| 8:30a | Dr. Fisher / Dr. Fowler — OBRIEN, Roman — In Pre-op — Sleeve Gastrectomy — 1110 | | |
| 9:00a | | Dr. Fisher / Dr. Willing — ALLEN, Paul — Inguinal Hernia | |
| 9:15a | | | XXXX, Xxxx — Dr. Toboggan — In Pre-op — Xxxxxx Xxxx |
| 9:30a | Dr. Fisher / Dr. Fowler — LARSON, Enzo — Scheduled — Gastric Bypass — 1112 | | |
| 10:00a | | Dr. Fisher / Dr. Willing — GILES, Wanda — Inguinal Hernia — 1118 — Canceled | |
| 10:30a | Dr. Fisher / Dr. Fowler — BRADFORD, Dana — Scheduled — Cholecystectomy — 1114 | | XXXX, Xxxx — Dr. Toboggan — Scheduled — Xxxxxx Xxxx |
| 10:45a | | Dr. Fisher / Dr. Fowler — HARVEY, Aminah — Gastric Bypass — Scheduled | |
| 11:30a | | | XXXX, Xxxx — Dr. Toboggan — Scheduled — Xxxxxx Xxxx |

SYSTEMS AND METHODS FOR ALLOWING REMOTE ROBOTIC SURGERY

CROSS-REFERENCE TO RELATED APPLICATIONS

This application claims priority to U.S. Provisional Patent Application No. 63/599,232, filed Nov. 15, 2023, and U.S. Provisional Patent Application No. 63/599,285, filed Nov. 15, 2023, each of which is incorporated by reference in its entirety. This application incorporates by reference in their entirety U.S. patent application Ser. Nos. 18/488,843, 18/488,844, and 18/488,886, filed Oct. 17, 2023 and titled "SYSTEMS AND METHODS FOR REMOTELY CONTROLLING ROBOTIC SURGERY." Any and all applications for which a foreign or domestic priority claim is identified in the Application Data Sheet as filed with the present application are hereby incorporated by reference under 37 CFR 1.57.

TECHNICAL FIELD

This disclosure relates generally to robotic surgery and more particularly to remotely controlling a plurality of robotic-assisted surgery systems.

DESCRIPTION OF RELATED ART

Robot-assisted surgery systems are generally available and have been developed to operate efficiently and safely. A robotic surgery system typically includes robotically actuable surgical instruments that may be inserted within the patient's body to perform a surgical procedure at a surgical site. The robotic surgery system is typically controlled by a surgeon via a surgeon input console, which is connected to the robotic surgery system via a control cable. The surgeon input console includes input devices that are grasped by the surgeon's hands and moved to generate signals for activating the surgical instruments to perform surgical operations at the surgical site. Signals are transmitted over the control cable to the robotic surgery system, which interprets the signals and generates control signals that cause the instruments to be actuated to perform surgical operations.

SUMMARY

Disclosed systems, apparatuses, and methods enable remotely controlling a plurality of robotic-assisted surgery systems. Such disclosed approaches provide a heterogeneous network for connecting remotely-located surgeon consoles and patient-side robotic surgery systems. Compatibility of a surgeon console with a patient-side robotic surgery system is verified prior to allowing the surgeon console to control the patient-side robotic surgery system to perform a surgical procedure. For surgeons, advantageously, remote surgery facilitates optimal utilization of their time and provides access to a sufficient volume of patients to perfect their skills. For patients, advantageously, remote surgery creates ample access to the right surgeon and the right care at an affordable price, decreases the need for travel, and reduces delayed care.

Further disclosed herein are systems, apparatuses, and methods for planning surgical sessions involving remotely located surgeon-side robotic surgical systems and patient-side robotic surgical systems. Such disclosed approaches provide a planning system for remotely located surgeons that allows each surgeon to operate a respective surgeon console to remotely control a respective plurality of patient-side robotic surgery systems to operate on a plurality of patients. Also disclosed herein are systems, apparatuses, and methods for allowing access for remotely controlling robotic surgery patient-side robotic surgery systems. Such disclosed approaches facilitate patient safety and increase the effectiveness of remotely controlled robotic surgery.

Other aspects and features will become apparent to those ordinarily skilled in the art upon review of the following description of specific disclosed implementations in conjunction with the accompanying figures.

BRIEF DESCRIPTION OF THE DRAWINGS

Specific implementations will now be described with reference to the following drawings, which are provided by way of example.

FIGS. 6A-1, 6A-2, 6B, and 6C are schematic views of remote surgery systems.

FIGS. 9A-9B illustrate user interfaces for planning surgical sessions.

DETAILED DESCRIPTION

Figure 1:
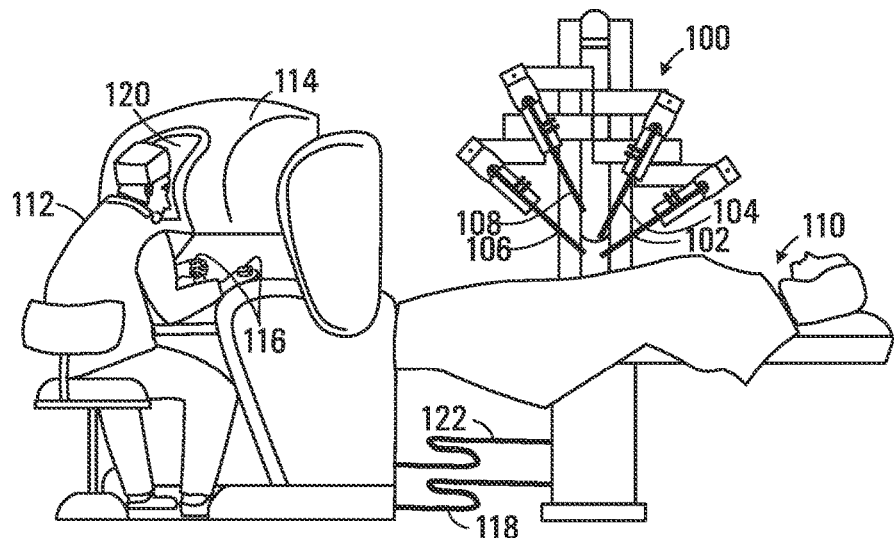
FIG. 1 is perspective view of a robotic surgery system.

Referring to FIG. 1, a robotic surgery system is shown generally at 100. The robotic surgery system 100 includes a plurality of robotically actuable surgical instruments 102-108 positioned on one or more robotic arms. At least one of the instruments 102-108 will generally be configured as an in-patient imaging system (such as, a camera, fluoroscopy system, radiography system, computer tomography (CT) system, ultrasound system, magnetic resonance imaging (MRI) system, or the like), which is inserted the body of the patient to generate images of anatomical structures and the surgical instruments 102-108 at a surgical site within the body of a patient 110. The remaining instruments may be configured to include an end effector that performs a specific surgical function (such as, forceps/graspers, needle drivers, scissors, electrocautery hooks, staplers, clip appliers, removers, etc.). The system 100 is controlled by a surgeon 112 via a surgeon input console 114, which is connected to the robotic surgery system 100 via a control cable 118. The surgeon input console 114 includes input devices (not shown) including handles 116 that are grasped by the surgeon's left and right hands and moved within an input device workspace or otherwise actuated to generate input signals. The input devices include encoders that transform positions and orientations of the handles 116 into input signal data representing the surgeon input. The input signals may thus be used for activating the plurality of surgical instruments 102-108 to perform surgical operations at the surgical site. The input signals are transmitted over the control cable 118 to the system 100, which interprets the signals and generates control signals that cause the instruments 102-108 to be actuated to move and perform other surgical operations. The input signals will generally be output by the input devices on the surgeon input console 114 as data signals representing the inputs to the console provided by the surgeon 112. For example, the surgeon input console 114 may generate input signals in the form of motion control signals that represent instantaneous positions of the handles 116 of the input devices within an input device workspace. The data signals are transmitted over the control cable 118, which is generally a wired connection between the surgeon input console 114 and the robotic surgery system 100. The wired connection ensures negligible transmission delay such that operations of the surgical instruments 102-108 caused by the surgeon will be effected by the system 100 with negligible delay. The control cable 118 may be implemented using any of a variety of different data transmission technologies such as Ethernet or Controller Area Network (CAN bus) protocol.

Additional input signals may also be generated at the surgeon input console 114. For example, the handles 116 may include other controls (not shown) that may be used to generate actuation signals that actuate operations at the surgical instruments 102-108, such as opening or closing a surgical scissor or forceps. The surgeon input console 114 may also include one or more foot pedals (not shown) that may be actuated by the surgeon to initiate various other operations. For example, a foot pedal may be configured to generate a clutch signal for temporarily decoupling the surgical instruments 102-108. A foot pedal may also be configured to initiate delivery of energy, such as generate electrocautery signals for initiating delivery of an electrocauterization current to an instrument, to cut, cauterize, or coagulate tissue (which can involve resection of tissue, vaporization of tissue, or coagulation of tissue). Delivery of energy can include delivery of ultrasonic energy (such as, with a harmonic scalpel instrument), delivery of electric energy (such as, with an electrocautery instrument), delivery of laser energy (such as, with a cautery instrument), delivery of radio frequency energy (such as, with a cautery instrument), or the like. These other input signals also need to be delivered to the robotic surgery system 100 to initiate their respective operations. Additionally, the robotic surgery system 100 may generate event-oriented notifications such as notifications of error conditions that must be communicated to the surgeon input console 114 to update the surgeon 112. Event-oriented messages may be time-sensitive, but are not necessarily synchronous.

The surgeon input console 114 also includes a display 120 for displaying images generated by the in-patient imaging system. The in-patient imaging system would generally be implemented as a high-resolution imaging system (such as, a video camera) that generates a stream of image frames. In some instances, the imaging system may generate images from differing perspectives that convey three-dimensional information and the display 120 may be configured as a stereoscopic display. The display signals generated by the imaging system are transmitted over an image transmission cable 122 back to the surgeon input console 114 for driving the display 120. The image transmission cable 122 is generally selected to ensure that the image frames are delivered to the display in near real-time so that the surgeon 112 does not perceive any delay between their hand movements and movements of the surgical instruments 102-108 represented on the display. In some implementations, the input signals and display signals may both be transmitted over a single shared cable or bus.

The robotic surgery system 100 may be housed within a sterile operating room that forms part of an operating suite. The surgeon or another surgeon aided by a perioperative nurse may make the necessary incisions and insert the instruments 102-108. The surgeon input console 114 may be housed in a portion of the operating suite that is separated from the operating room so that the surgeon operating the input console need not wear surgical gloves while manipulating the controls of the input console. The cables 118 and 122 would generally extend through a port in a wall between the surgeon input console 114 and the robotic surgery system 100. In cases where another surgeon performs the incisions in the body of the patient 110, the operating surgeon may not need to complete the full process of scrubbing, gowning, and gloving before the operation. In this situation, the surgeon input console 114 however remains in a direct wired connection with the robotic surgery system 100 via the cables 118 and 122. The direct wired connection ensures that the robotic surgery system 100 is able to rapidly respond to the surgeon's inputs provided at the surgeon input console 114 and the display 120 displays images of the surgical site with a negligible delay that is virtually unnoticeable to the surgeon.

Overview of Remotely Controlling Robotic Surgery

One of the main problems in the healthcare industry is the lack of surgeons and underutilization of surgeons. On one hand, there is a lack of high-quality surgeons. For instance, a 2022 article by the American College of Surgeons concludes that there is an acute ongoing shortage of surgeons available in the United States to serve the patient population. The shortage of high-quality surgical care is particularly severe in rural areas. In addition, surgeons in many geographical areas may not have access to a sufficient volume of patients to perfect their surgical skills because the population is not evenly distributed, thus creating a lack of surgical volume in such areas. On the other hand, currently there are severe inefficiencies with utilizing the time of surgeons. Surgeons are required to travel between different hospitals, some of which may be located in difficult to reach places or between different operating rooms in a single hospital. Moreover, surgeons are required to wait for patients and operating rooms to be prepared for surgery. This results in a serious underutilization of surgeons' time. There are many advantages in allowing surgeons to control robotic surgery systems (such as, the system 100) from remote locations in order to increase efficiency and improve patient care. For surgeons, remote surgery facilitates optimal utilization of their time and provides access to a sufficient volume of patients to perfect their skills. For patients, remote surgery creates ample access to the right surgeon and the right care at an affordable price, decreases the need for travel, and decreases delayed care. However, there are a number of challenges with designing a system that would allow remotely controlling robotic surgery systems. These include transmission delay and reliability of transmission.

Figure 2:
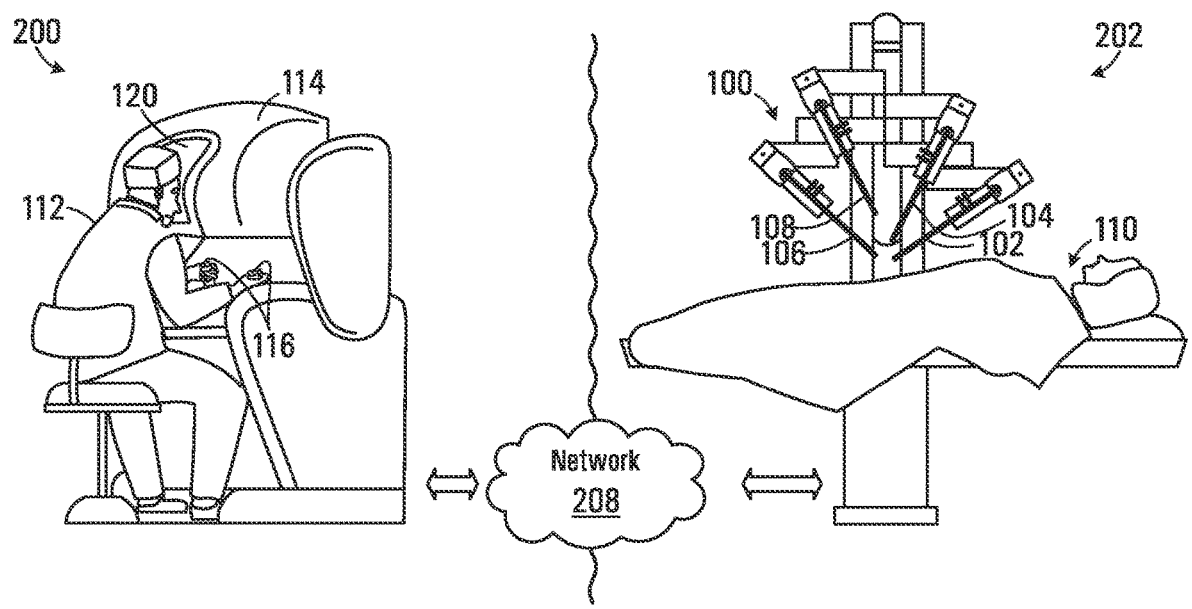
FIG. 2 is perspective view of a robotic surgery system.

Referring to FIG. 2, the surgeon input console 114 is disposed at a surgeon-side location 200 and the robotic surgery system 100 shown in FIG. 1 is disposed at a patient-side location 202. The surgeon-side location 200 is remote from the patient-side location 202 to an extent where a directly wired connection between the robotic surgery system 100 and the surgeon input console 114 is no longer possible. Advantageously, the surgeon-side location 200 may be in another building or even another city, state, or country. In this example, communications are conducted between the surgeon-side location 200 and the patient-side location 202 via a network 208 and there is no direct wired connection between the surgeon input console 114 and the robotic surgery system 100.

Figure 3:
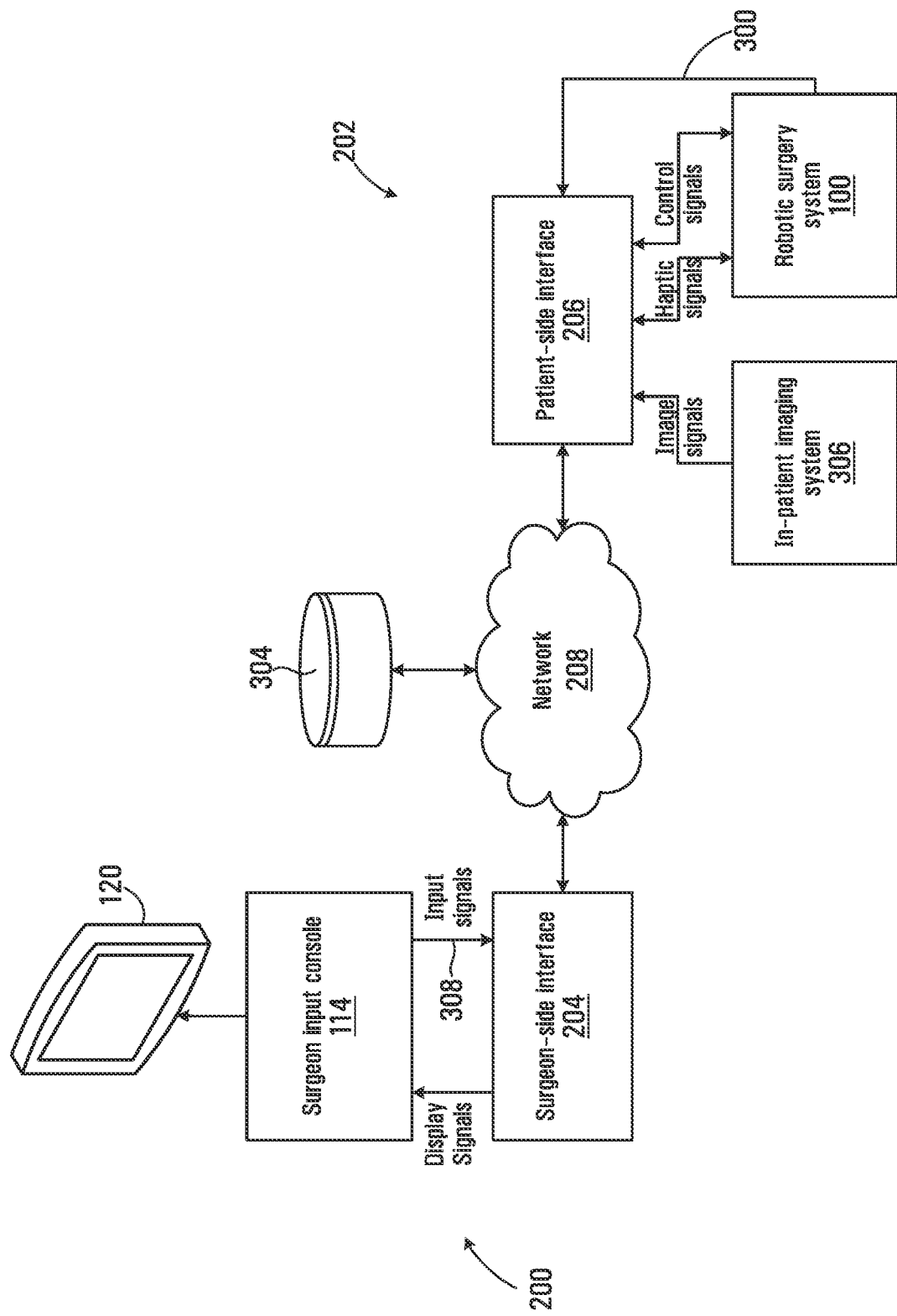
FIG. 3 is a block diagram of components of the robotic surgery system of FIG. 2.

Referring to FIG. 3, communication between the surgeon-side location 200 and patient-side location 202 are conducted via a surgeon-side interface 204 and a patient-side interface 206, which are shown schematically in FIG. 3. The surgeon-side interface 204 is connected to receive input signals from the surgeon input console 114. For example, the surgeon input console 114 may generate a stream of motion input signals 308 that represent the instantaneous position of the handles 116 within an input console workspace. Motion input signals can represent a desired movement (including position and velocity) of an instrument in the input console workspace. These motion input signals will generally be transformed via kinematic processing into signals representing desired positions and orientations of the joints of the instruments 102-108 within a surgical workspace of the robotic surgery system 100. In some instances, kinematic processing translates the position and movement of the handles 116 within the input console workspace into the position and movement of joints of the instruments 102-108. The translation can be performed by transforming the position and orientation of the handles 116 in the Cartesian coordinate system to the coordinates of the joints of the instruments 102-108 in the surgical workspace and vice versa. Other processing functions may then be used to transform these kinematically derived instrument joint positions into drive signals for actuating various actuators, such as motor servos, that cause movement of the instruments 102-108 within the surgical workspace. In the system shown in FIG. 1, the kinematic and other processing may be implemented within the surgeon input console 114 or the within robotic surgery system 100. In the implementation of FIG. 3, the input signals 308 can be picked up directly from the input devices of the surgeon input console 114 and before any kinematic or other processing has been performed. For some robotic surgery system 100, the input signals are generated by the input devices of the surgeon input console 114 at a relatively low frequency (or rate of change), for example about 200 Hz or every 5 milliseconds or about 30 Hz or less. The input signals 308 thus require a relatively low bandwidth or data rate for transmission. In contrast, post-kinematics and other processing signals may have a significantly higher frequency (or rate of change). As an example, in some robotic surgery systems the servo rate at the motor controller may be in the region of about 10 kHz or more, which may require a significantly higher bandwidth or data rate for transmission than the motion input signals generated at the input device.

In general, remotely controlling a robotic surgery system can be achieved by transmitting from the surgeon-side interface 204 to the patient-side interface 206 a complete set of signals that control the instruments 102-108 (which include at least one imaging system). To reduce delay and guarantee reliability of the transmission, such set of signals can include signals having the lowest frequency (or rate of change) among a plurality of available signals. As described above, input signals 308 can be transmitted from the surgeon-side interface 204 to the patient-side interface 206, rather than signals generated as a result of kinematic processing that generates signals representing desired coordinates of the joints of the instruments 102-108 in the surgical workspace associated with the robotic surgery system 100 or the drive signals (such as, torque) for actuating the motors of the instruments 102-108. In some cases, the surgeon-side interface 204 can select input signals 308 for transmission from the plurality of available signals, which can include signals generated as a result of kinematic processing and the drive signals.

In certain implementations, one or more signals generated as a result of kinematic processing may be transmitted by the surgeon-side interface 204 to the patient-side interface 206. These signals can be transmitted along the input signals 308.

The surgeon-side interface 204 is in communication with the patient-side interface 206 over the network 208. The patient-side interface 206 is in communication with the robotic surgery system 100 for receiving and delivering control signals to the robotic surgery system. The patient-side location 202 also includes an in-patient imaging system 306, which generates images of the surgical site within the patient. As described above, one of the surgical instruments 102-108 may be configured to generate the in-patient images or a separate imaging system may be employed. The in-patient imaging system 306 generates data representing image frames, which is encoded into an image data stream by the patient-side interface 206 and transmitted over the network 208 to the surgeon-side interface 204. The surgeon-side interface 204 receives and decodes the image data stream to recover the image frame data, which is sent via the surgeon input console 114 to the display 120 associated with the surgeon input console 114. The surgeon 112 is able to view the surgical site on the display 120 and cause movements of the handles 116 of the surgeon input console 114, which are encoded by the input devices and delivered as input signals to the patient-side interface 206.

The robotic surgery system 100 may be additionally configured to generate haptic feedback and/or force feedback signals. In robotic surgery, haptic feedback signals may be generated to alert the surgeon 112 when an attempt is made to move one of the instruments 102-108 against an instrument movement boundary or other impediment to motion. Haptic signals may also be generated when two of the instruments 102-108 are moved toward a collision condition. These haptic signals are generally used to deliver haptic feedback via the handles 116 of surgeon input console 114 that alert the surgeon 112 to the condition. Additionally, some robotic systems may also be configured to generate force feedback signals that can be used to deliver force feedback to the surgeon via the input console 114. The force feedback may serve to indicate that the surgeon 112 is attempting to move one of the instruments 102-108 against a limitation such as human tissue or an organ. In some implementations the patient-side interface 206 may be configured to receive the haptic or force feedback signals and transmit the signals back to the surgeon-side interface 204 for delivery to the surgeon input console 114.

The network 208 may be provided as a connection to the internet. In some cases, the network 208 may be a dedicated network such as a point-to-point fiber or a specially-conditioned and monitored network that aims to reduce transmission delay and increase reliability and stability. The surgeon-side interface 204 is in communication with the robotic surgery system 100 at the patient-side location 202 via the network 208.

The surgeon-side interface 204 can be integrated with the surgeon input console 114, which can encompass being wholly separate from the surgeon input console 114 or being wholly or partially a portion of the surgeon input console 114. In some implementations, the surgeon-side interface 204 can be implemented as software and/or firmware being executed by one or more processors of the surgeon input console 114.

The patient-side interface 206 can be integrated with the robotic surgery system 100, which can encompass being wholly separate from the robotic surgery system 100 or being wholly or partially a portion of the robotic surgery system 100. In some implementations, the patient-side interface 206 can be implemented as software and/or firmware being executed by one or more processors of the robotic surgery system 100.

System for Remotely Controlling Robotic Surgery

Figure 4:
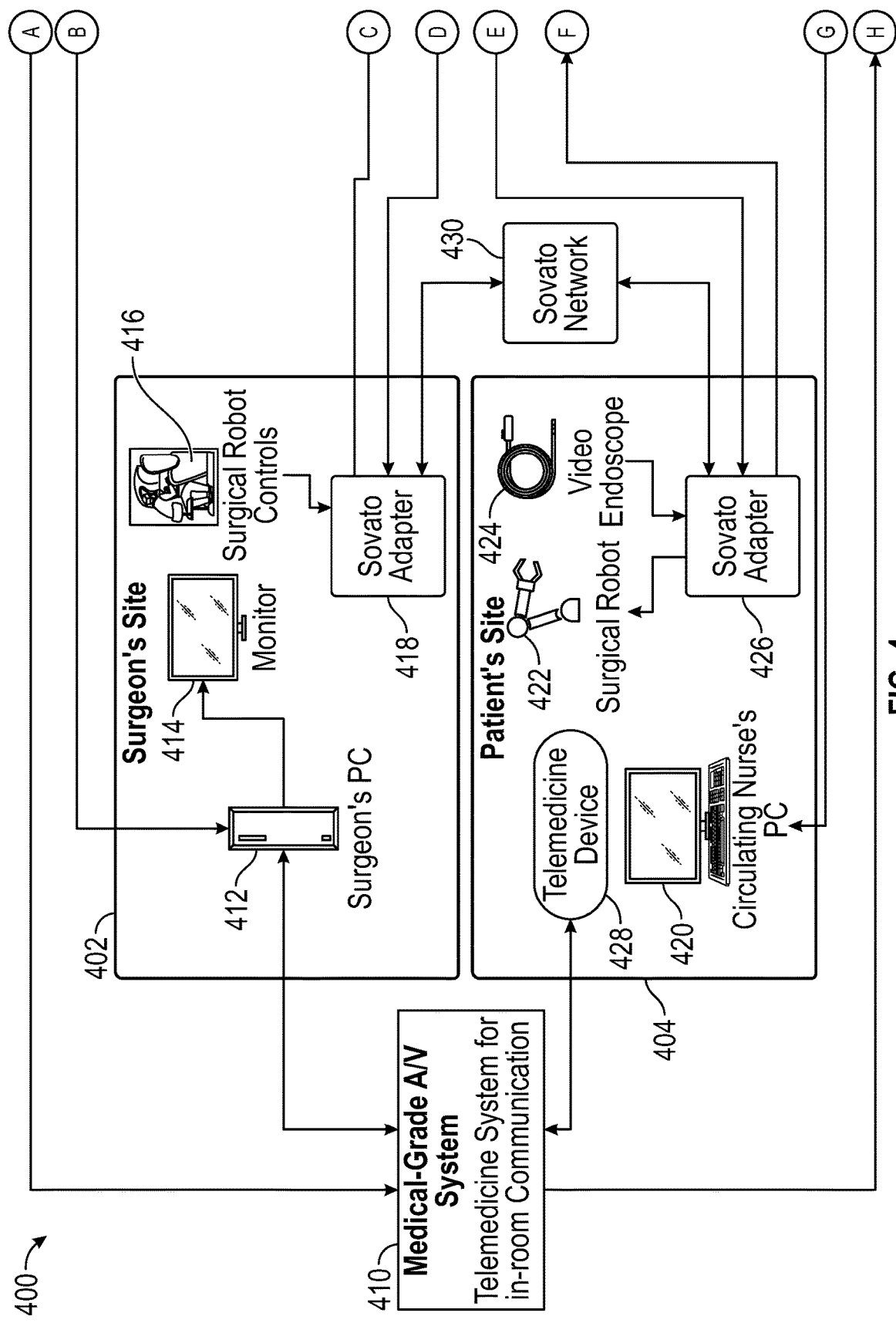
FIG. 4 is a schematic view of a remote surgery system.
Figure 4:
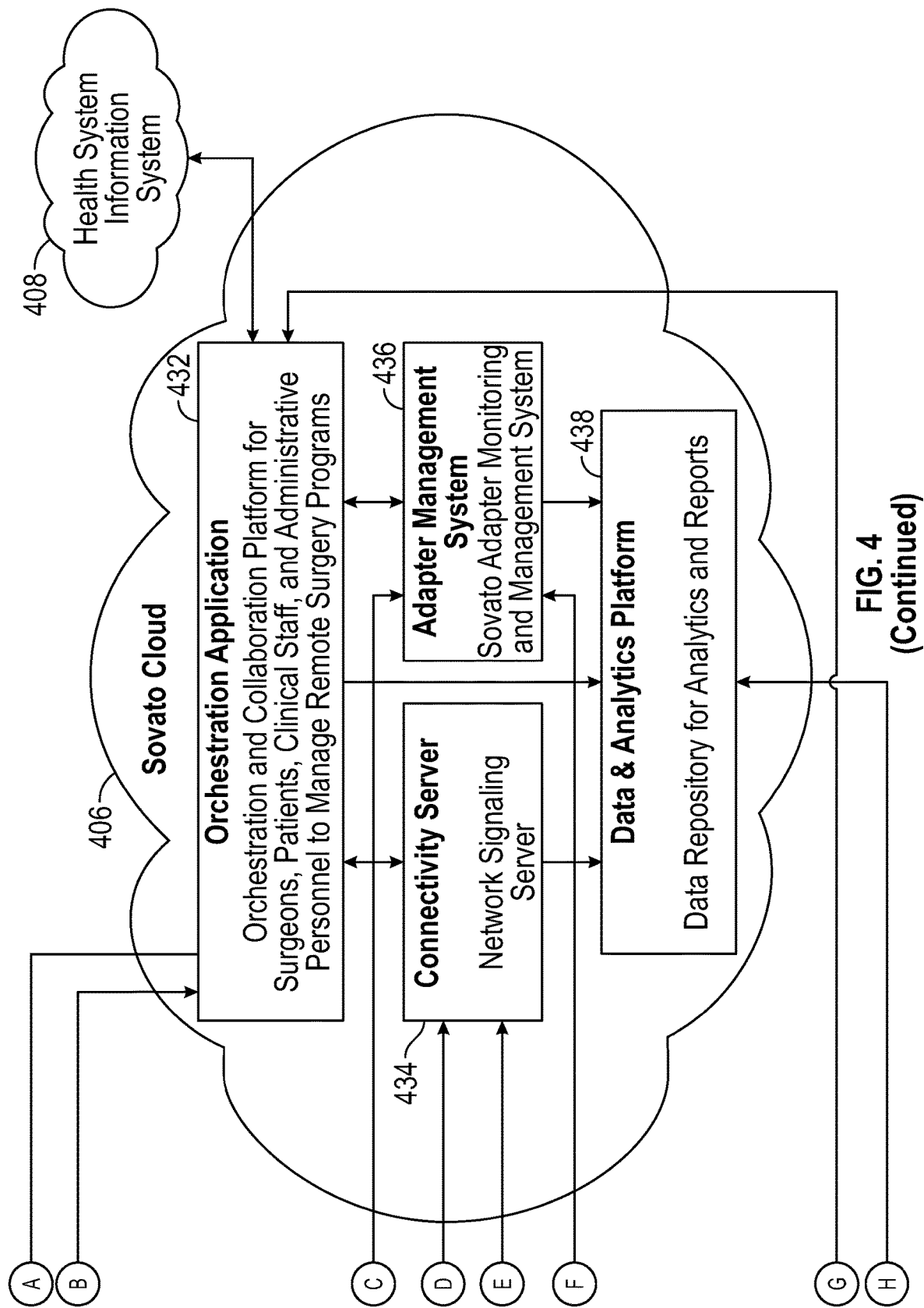

FIG. 4 illustrates a schematic view of a remote surgery system 400. The system 400 can include one or more surgeon sites 402 having one or more computing devices 412 (such as, one or more surgeon personal computers (PCs)), one or more monitors 414 (which can be connected to the one or more surgeon PCs), surgical robot control and display system 416 (which can be same as or similar to the surgeon input console 114 and can be referred to as a surgeon input console 416), and surgeon-side adapter 418 (which can be same as or similar to the surgeon-side interface 204). Any of the computing devices described herein can be mobile or portable.

The system 400 can further include one or more patient sites 404 having one or more computing devices 420 (such as, one or more nurse PCs), a surgical robot 422 (which can be same as or similar to the robotic surgery system 100), one or more imaging systems 424 (such as, a video endoscope), and patient-side adapter 426 (which can be same as or similar to the patient-side interface 206). The system 400 can also include a telemedicine device 428 configured to communicate telemedicine information and provide the surgeon with audio and video related to any procedures the surgeon is performing. The system 400 can further include a network 430 (which can be same as or similar to the network 208) connecting the surgeon-side adapter 418 to the patient-side adapter 426.

The system 400 can include one or more computing devices 406, which can form a computing cloud. The cloud can implement one or more of: an orchestration application 432, a connectivity server 434, an adapter management system 436, and a data and analytics platform 438. The system 400 can further include a health system information systems 408, comprising a database storing electronic health records (EHR) and/or electronic medical records (EMR) relating to one or more patients. The system 400 can further include a medical-grade audio/visual (A/V) system 410, which can communicate with the telemedicine device 428.

A surgeon PC 412 can be operably connected to the medical-grade A/V system 410 and the orchestration application 432. In an example, the surgeon PC 412 can communicate telemedicine information and provide the surgeon with audio and video related to any surgical procedures the surgeon is conducting. For example, the surgeon PC 412 can display to the surgeon on a monitor 414 a real-time video of a patient site 404, the operation facilities where a surgery will take place, is being performed, or has been performed. The monitor 414 can display such footage in response to the medical-grade A/V system 410 providing video footage of the patient site 404 to the surgeon site 402. The surgeon PC 412 can also be operably connected to the orchestration application 432. The surgeon PC 412 can transmit surgeon related information to the orchestration application 432. The surgeon related information can include information such as the surgeon's credentials, identification, schedule, specialties, and any access related information related to the procedures the surgeon will perform.

The surgeon input console 416 can include a visual display to show the surgeon visual indications relating to the remote surgery. The surgeon input console 416 can be operably coupled to the surgeon-side adapter 418. The surgeon input console 416 can display a view of the surgical site (for instance, as detected by an imaging system 424) and/or any other component relevant to surgery. The monitor 414 can display visual indicators representing a strength of signal connectivity to the components in the patient site 404. In another example, the monitor 414 can display device characteristics regarding the surgeon input console 416 and/or the surgical robot 422.

As described in connection with the surgeon input console 114, the surgeon input console 416 can include one or more devices used to control one or more surgical robots. The surgeon input console 416 can be operably coupled to the surgeon-side adapter 418. In an example, surgical robot controls of the surgeon input console 416 can control movement, actuation, clutch, or any other relevant feature for a surgical robot to perform surgery. The surgeon input console 416, and the corresponding console, can include a type. The type can correspond to the manufacturer of the surgeon input console, model of the surgeon input console, and/or version of the software or firmware being executed by one or more processors or the surgeon input console 416. For example, the manufacturer of the surgeon input console 416 can include Intuitive Surgical, Medtronic, or any other manufacturer of surgeon input console. As another example, the model of the surgeon input console 416 can include Da Vinci Xi, Da Vinci X, or Da Vinci SP manufactured by Intuitive Surgical.

The surgeon-side adapter 418 can include a physical device, program, application, application programming interface (API), software development kit (SDK), or another device or program to allow remote surgery. In some implementations, the surgeon-side adapter 426 can be software and/or firmware being executed by one or more processors of the surgeon input console 416. The surgeon-side adapter 418 can be operably coupled to the patient-side adapter 426 via the network 430 and/or the cloud 406, including the connectivity server 434 and the adapter management system 436. In an example, the surgeon-side adapter 418 can include a device operably coupled to the surgeon input console 416, to interface the surgeon input console 416 to the cloud 406 and the network 430. In this example, the surgeon-side adapter 418 can include hardware components and software components to receive communication signals from the surgeon input console 416 and establish a network connection to the network 430 and the cloud 406. In this example, the surgeon-side adapter 418 can include an internal internet protocol (IP) address and an external IP address. The internal IP address can correspond to an IP address with respect to a local network of the surgeon site 402. The external IP address can correspond to an IP address outside of that local network. The surgeon-side adapter 418 can communicate with the cloud 406 and/or the network 430 and provide information (such as, the external IP address and the external IP address) to initiate a connection with the patient-side adapter 426. The information to initiate a connection with the patient-side adapter 426 can include an identifier of the surgeon-side adapter 418, an internal IP address of the surgeon-side adapter 418, an external IP address of the surgeon-side adapter 418, and/or any or information relevant to establish a connection with the patient-side adapter 426.

The surgeon-site adapter 418 and/or the patient-side adapter 426 can be configured software-defined wide-area network (SD-WAN) devices. The network 430 can be configured as SD-WAN network connecting such SD-WAN devices. Internal IP addresses can be used to communicate with devices on the SD-WAN. The internal IP address of the surgeon-site adapter 418 and/or the patient-side adapter 426 can be used to establish the connection for remote surgery since the adapters would part of the same WAN, and external IP addresses may not need to be used. Any other components of the system 400, such as the A/V system 410, surgeon PC 412, nurse PC 420, or telemedicine device 428, can be similarly configured as SD-WAN devices and become part of the SD-WAN.

The nurse PC 420 can also be operably connected to the orchestration application 432. The nurse PC 420 can transmit patient related information to the orchestration application 432. The patient related information can include the patient's health records, identification, schedule, notes, and any access related information related to the procedures the patient can receive.

The surgical robot 422 can include one or more robotic devices used to perform surgery. The surgical robot 422 can be operably coupled to the patient-side adapter 426. In an example, the surgical robot 422 can receive controls to perform movement, actuation, power, and any other relevant feature for a surgical robot to perform surgery. The surgical robot 422, and any corresponding devices, can include a type. The type can correspond to the manufacturer of the surgical robot, model of the surgical robot, and/or version of the software or firmware being executed by one or more processors of the surgical robot 422. For example, the manufacturer of the surgical robot 422 can include Intuitive Surgical, Medtronic, or any other manufacturer of surgical robots. As another example, the model of the surgical robot 422 can include Da Vinci Xi, Da Vinci X, or Da Vinci SP manufactured by Intuitive Surgical.

The imaging system 424 can communicate video to the surgeon related to any procedures the surgeon is performing. The imaging system 424 can be operably coupled to the patient-side adapter 426 (directly or through the surgical robot 422). In an example, the imaging system 424 can provide to the surgeon site 402 a view of the surgical site. The view can include a real-time perspective of the patient before, during, or after surgery is performed.

The patient-side adapter 426 can be operably coupled to the surgeon-side adapter 418 via the network 430 and/or the cloud 406. The patient-side adapter 426 can include one or more of a physical hardware, program, application, API, SDK, or another device or program to allow remote surgery. For example, patient-side adapter 426 can include a device operably coupled to the surgical robot 422, to interface the surgical robot 422 to the cloud 406 and the network 430. In this example, the patient-side adapter 426 can include hardware components and software components to receive communication signals from the surgical robot 422 and establish a network connection to the network 430 and the cloud 406. In some implementations, the patient-side adapter 426 can be software and/or firmware being executed by one or more processors of the surgical robot 422. Similarly to the surgeon-side adapter 418, the patient-side adapter 426 can include an internal IP address and an external IP address. As described herein, one or more of such IP addresses can be utilized to establish a connection with the surgeon-side adapter. The information to initiate a connection with the surgeon-side adapter 418 can include an identifier of the patient-side adapter 426, an internal IP address of the patient-side adapter 426, an external IP address of the surgeon-side adapter 418, and/or any or information relevant to establish a connection with the patient-side adapter 426. As described herein, the patient-side adapter 426 can be configured as SD-WAN device and its internal IP address can be used to establish the connection.

The telemedicine device 428 can communicate telemedicine information and provide the surgeon with audio and video related to any procedures the surgeon is performing. The telemedicine device 428 can be operably coupled to the medical-grade A/V system 410. In an example, the telemedicine device 428 can provide to the surgeon site 402 a view of the patient site 404 (such as, an operating room). The view can include a real-time perspective of the patient before, during, or after surgery is performed. In another example, the telemedicine device 428 can receive information from the surgeon PC 412 through the medical-grade A/V system 410. For example, the telemedicine device 428 can receive information related to the surgery, including one or more of a notice regarding the surgeon's readiness, status of connectivity, updated patient health records, or scheduling information. In this example, the related information can include the surgeon's credentials, identification, schedule, specialties, and any access related information related to the procedures the surgeon will perform. In another example, the telemedicine device 428 can further include an A/V system including a third-party telemedicine hardware provider and medical cart. The A/V system 410 and/or the telemedicine device 428 can facilitate provision of an audio and/or video feed from the patient site 404 to the surgeon site 402 (and vice versa) as well as facilitate a two-way audio and/or video communication between the patient site 404 and the surgeon site 402.

The network 430 can connect the surgeon-side adapter 418 and the patient-side adapter 426. The network 430 can be configured as a software defined-wide area network (SD-WAN) to provide connectivity between the surgeon-side adapter 418 and the patient-side adapter 426. The network 430 can facilitate a peer-to-peer connection between the surgeon-side adapter 418 and the patient-side adapter 426. Such peer-to-peer connection can allow the surgeon-side adapter 418 and the patient-side adapter 426 to transmit and receive information and instructions (such as, in the form of data packets) directly. The information can include surgical robot control instructions and feedback sensor information, real-time patient information including medical health monitoring statuses, patient-side video endoscope content (for example, from the video endoscope 424), network connectivity strength including a primary and alternate network connectivity options (for example, SD-WAN, 5G, Ethernet, fiber optic, satellite communication, or any other type of connection available), and any other information relevant to the peer-to-peer network connection.

There can be several ways for establishing a connection via the network 430. For example, the surgeon-side adapter 418 can request connection to the patient-side adapter 426 from the connectivity server 434. For example, the surgeon-side adapter 418 can transmit a request to the connectivity server 434 and receive the patient-side adapter 426 internal IP address from the connectivity server 434. In this example, the surgeon-side adapter 418 can then request to establish a connection (such as, a direct peer-to-peer connection) with the patient-side adapter 426.

As another example, the surgeon-side adapter 418 can request a connection to the patient-side adapter 426 from the adapter management system 436. For example, the surgeon-side adapter 418 can transmit a request to the connectivity server 434 and receive the patient-side adapter 426 internal IP address from the adapter management system 436. In this example, the surgeon-side adapter 418 can then request to establish a connection (such as, a direct peer-to-peer connection) with the patient-side adapter 426. While these examples describe that the surgeon-side adapter 418 initiates the connection to the patient-side adapter 426, the patient-side adapter 426 can similarly initiate the connection in some implementations.

In any of these examples, external IP address(es) can also be used to establish the connection. As described herein, external IP address(es) can be used when the adapters are not part of the same network (such as, not part of the same SD-WAN).

In some implementations, the network 430 can facilitate server-based connectivity (rather than peer-to-peer connectivity). For example, both adapters 418 and 420 can transmit data packets through the connectivity server 434 to communicate with each other.

In some examples, the system 400 can assess whether a type of a surgical robot 422 is compatible with a surgeon input console 416. In this example, the system 400 will compare the types of the surgical robot 422 and the surgeon input console 416 to ensure the types are compatible (such as, the same) prior to providing information to establish a connection between the surgical robot 422 and the surgeon input console 416. In this example, when the surgical robot 422 is of a first type and the surgeon input console 416 are of the first type, the system 400 will provide over the network 430 information to one or both of the surgical robot 422 and the surgeon input console 416 to allow the devices to establish a connection (such as, a peer-to-peer connection) for remotely controlling the surgical robot 422. Such connection can be established between the surgeon-side adapter 418 and the patient-side adapter 426. In another example, when the surgical robot 422 is of a first type and the surgeon input console 416 are of a second type that is different from the first type, the system 400 will restrict provision of the information over the network 430 and prevent the devices from establishing the connection.

It should be noted that a preliminary maintenance connection may be formed via the network 430 between the surgeon-side adapter 418 and the patient-side adapter 426 prior to forming the operational connection for remotely controlling the surgical robot 422. The preliminary maintenance connection can be used by the surgeon-side adapter 418 and the patient-side adapter 426 for exchanging information related to discovery, status, keeping the preliminary connection alive, or the like. This type of connection can be distinct from an operational connection (where the operational connection may be otherwise known as a "session") for remotely controlling the surgical robot 422 during which the following types of data would be transmitted: control signals (or control commands) transmitted from the surgeon side to the patient side for moving and/or actuating one or more instruments or imaging systems of the surgical robot 422, status information transmitted from the patient side to the surgeon side (such as, heartbeat signal or other data for ensuring safety), and image data of the surgical site transmitted from the patient side to the surgeon side. When the operational connection for remotely controlling the surgical robot 422 is established between the surgeon-side adapter 418 and the patient-side adapter 426, all these three types of data would be exchanged between the surgeon side and patient side.

In some instances, the connection for remotely controlling the surgical robot 422 would not be established (and the three types of data described herein would not be exchanged) unless there has been coordination between the patient side and surgeon side. Coordination can include one or more of performing safety checks (such as, compatibility between the types of the surgeon input console 416 and the surgical robot 422), ensuring that the operating room and surgical robot 422 have been prepared for surgery, ensuring that the patient has been prepared for surgery, or the like. In some cases, coordination can be performed by the system 400 and may include completion of or more checklists on the patient side (for instance, by a circulating nurse) and attestation by the surgeon that the one or more checklists have been completed correctly (such as, by clicking "Attest" on a user interface displayed on the monitor 414). A checklist can be completed on the nurse PC 420, transmitted to the surgeon side via the network 430, displayed on the surgeon PC 412, and attested to by the surgeon through the surgeon PC 412.

In some instances, at least some types of data related to the connection may be transmitted prior to establishing the connection for remotely controlling the surgical robot 422. For example, image data of the surgical site may be transmitted to help the surgeon prepare for the surgery (such as, plan the surgery). Transmission of control signals and status information may be commenced at the same time.

The orchestration application 432 can include an orchestration and collaboration platform for surgeons, patients, clinical staff, and administrative personnel to manage remote surgery programs. The orchestration application 432 can be executed on one or more remote servers in the cloud 406 and can be operably connected to the health system information systems 408, the A/V system 410, the surgeon PC 412, nurse PC 420, connectivity server 434, the adapter management system 436, and the data and analytics platform 438. In some examples, the orchestration application 432 is configured to assess whether a type of a surgical robot 422 is compatible with a surgeon input console 416.

The assessment of compatibility can occur prior to or at a time of a surgery. For example, the system 400 (such as, via the orchestration application 432) can assess the compatibility at the time the surgery is scheduled, which can be well before the time of surgery (such as, hours, days, or weeks) and well before the connection for remotely controlling the surgical robot 422 is established between the adapters 418 and 426. As a safety check, compatibility may be verified again prior to forming the connection.

In another example, the system 400 can assess compatibility at the time of surgery (such as, close to the initiation of the connection). This can be performed minutes or even seconds prior to the surgery.

The process for the orchestration application 432 to assess the compatibility between the surgical robot 422 and the surgeon input console 416 can be an automated process, where there is no user intervention to begin the assessment of the compatibility. As described herein, for example, the orchestration application 432 can pre-verify compatibility of the types prior to when the connection for remotely controlling the surgical robot 422 is established.

The system 400 (such as, via the orchestration application 432) can compare the types of the surgical robot 422 and the surgeon input console 416 to ensure the types are compatible prior to establishment of the connection for remotely controlling the surgical robot 422. For example, when the surgical robot 422 is of a first type and the surgeon input console 416 are of the first type, the orchestration application 432 can provide over the network 430 information to one or both of the patient-side adapter 426 and surgeon-side adapter 418 to allow the devices to establish a connection (such as, a peer-to-peer connection). In another example, when the surgical robot 422 is of a first type and the surgeon input console 416 are of a second type that is different from the first type, the orchestration application 432 will restrict provision of the information over the network 430 and prevent the devices from establishing the connection.

The connectivity server 434 can include a network signaling server. The connectivity server 434 can be operably coupled to the surgeon-side adapter 418, the patient-side adapter 426, the orchestration application 432, and the data and analytics platform 438. The connectivity server 434 can provide a service of connecting the surgeon-side adapter 418 and the patient-side adapter 426.

For example, the connectivity server 434 can receive a request from the surgeon-side adapter 418 to establish a connection with the patient-side adapter 426 (or vice versa). In this example, the connectivity server 434 can obtain the surgeon-side adapter 418 information, including an identifier, an external IP address (if needed), an internal IP address and patient-side adapter 426 information, including an identifier, an external IP address (if needed), and an internal IP address. The connectivity server 434 can obtain the surgeon-side adapter 418 information from the surgeon-side adapter 418 and/or from the adapter management system 436. In this example, the connectivity server 434 can also receive an identifier of the patient-side adapter 426 from the surgeon-side adapter 418, indicating the patient-side adapter 426 with which to establish a connection. The connectivity server 434 can then transmit a request to the patient-side adapter 426, to determine whether the patient-side adapter 426 is capable of establishing a connection to the surgeon-side adapter 418 over the network 430. In response to receiving an approval from the patient-side adapter 426, the connectivity server 434 can transmit the patient-side adapter 426 information to the surgeon-side adapter 418 to allow the surgeon-side adapter 418 to establish a connection between the adapters (for example, via the network 430). In this example, the connectivity server 434 can transmit the patient-side adapter 426 identifier, internal IP address, and external IP address (if needed). The connectivity server 434 can provide a threshold security procedure to assess whether the surgeon-side adapter 418 has authorization to establish a connection with the patient-side adapter 426. In this example, the connectivity server 434 can include an access control list of authorized adapters and compare the identifier of the surgeon-side adapter 418 to verify authorization.

In another example, the connectivity server 434 can receive a request from the patient-side adapter 426 to establish a connection with the surgeon-side adapter 418. The connectivity server 434 can also obtain the patient-side adapter 426 information, including an identifier, an external IP address (if needed), an internal IP address and patient-side adapter 426 information, including an identifier, an external IP address (if needed), and an internal IP address. The connectivity server 434 can obtain the patient-side adapter 426 information from the patient-side adapter 426 and/or from the adapter management system 436. The connectivity server 434 can also receive an identifier of the surgeon-side adapter 418 from the patient-side adapter 426, indicating the surgeon-side adapter 418 with which to establish a connection. The connectivity server 434 can then transmit a request to the surgeon-side adapter 418, to determine whether the surgeon-side adapter 418 is capable of establishing a connection to the patient-side adapter 426 over the network 430. In response to receiving an approval from the surgeon-side adapter 418, the connectivity server 434 can then transmit the surgeon-side adapter 418 information to the patient-side adapter 426 to allow the patient-side adapter 426 to establish a connection between the adapters (for example, via the network 430). In this example, the connectivity server 434 can transmit the surgeon-side adapter 418 identifier, internal IP address, and external IP address (if needed). The connectivity server 434 can provide a threshold security procedure to assess whether the patient-side adapter 426 has authorization to establish a connection with the surgeon-side adapter 418. In this example, the connectivity server 434 can include an access control list of authorized adapters and compare the identifier of the patient-side adapter 426 to verify the authorization.

In another example, the connectivity server 434 can receive a request from the orchestration application 432 to establish a connection between the surgeon-side adapter 418 and the patient-side adapter 426. The connectivity server 434 can obtain the surgeon-side adapter 418 information, including an identifier, an external IP address (if needed), an internal IP address and patient-side adapter 426 information, including an identifier, an external IP address (if needed), and an internal IP address. The connectivity server 434 can obtain the information from the adapters and/or from the adapter management system 436. For instance, the connectivity server 434 can receive the patient-side adapter 426 identifier from the orchestration application 432 to establish a connection between the patient-side adapter 426 and the surgeon-side adapter 418. The connectivity server 434 can then transmit a request to the surgeon-side adapter 418 to determine whether the surgeon-side adapter 418 is capable of establishing a connection to the patient-side adapter 426 over the network 430. In response to receiving approval from the surgeon-side adapter 418, the connectivity server 434 can then transmit the surgeon-side adapter 418 information to the patient-side adapter 426 to allow the surgeon-side adapter 418 to establish a connection between the adapters (for example, via the network 430). In this example, the connectivity server 434 can transmit the surgeon-side adapter 418 identifier, internal IP address, and external IP address (if needed) for the patient-side adapter 426 to establish a connection with the surgeon-side adapter 418. The connectivity server 434 can provide a threshold security procedure to assess whether the adapters have authorization to establish a connection across the network 430. The connectivity server 434 can include an access control list of authorized adapters and compare the identifiers of the adapters to verify authorization.

The adapter management system 436 can provide adapter monitoring and management. The adapter management system 436 can be operably coupled to the surgeon-side adapter 418, the patient-side adapter 426, the orchestration application 432, and the data and analytics platform 438. In an example, the adapter management system 436 can store information regarding adapters connected to the cloud 406. The information stored can include identifiers, internal IP addresses, and external IP addresses (if needed) of the adapters. In this example, the adapters connected to the cloud 406 are in a trusted state (for instance, part of the same SD-WAN), such that the adapter management system 436 communicates directly with the adapters. In this example, the adapter management system 436 can communicate with the adapters as if the adapters are on the same local network, such that there is no need to communicate using an external IP address, as described herein.

The data and analytics platform 438 can include a data repository for analysis and reports, which can improve the performance of the surgery teams and technology that facilitates remote surgery. The data and analytics platform 438 can be operably coupled to the medical-grade A/V system 410, the orchestration application 432, the connectivity server 434, and the adapter management system 436. The data and analytics platform 438 can store data from remote surgery procedures performed using the system 400.

The aforementioned components of the system 400 (such as, one or more of the health system information systems 408, the medical-grade A/V system 410, the surgeon PC 412, the monitor 414, surgeon input console 416, surgeon-side adapter 418, nurse PC 420, surgical robot 422, imaging system 424, patient-side adapter 426, the cloud 406, the orchestration application 432, the connectivity server 434, the adapter management system 436, or the data and analytics platform 438) can be communicably coupled to each other via the network 430 and/or the cloud 406, such that data can be transmitted between the components. The network 430 and the cloud 406 can include the Internet, intranet, or other suitable network. The data transmission can be encrypted, unencrypted, over a virtual private network (VPN) tunnel, or other suitable communication means. The network 430 and the cloud 406 can be a wide area network (WAN) (such as, SD-WAN), local area network (LAN), personal area network (PAN), or another suitable network type. The network communication between any of the system 400 components can be encrypted using pretty good privacy (PGP), Blowfish, Twofish, triple data encryption standard (3DES), hypertext transfer protocol secure (HTTPS), or other suitable encryption. The system 400 can be configured to provide communication via the various systems, components, and modules disclosed herein via an application programming interface (API), peripheral component interface (PCI), PCI-Express, American National Standards Institute (ANSI)-X12, Ethernet, Wi-Fi, Bluetooth, or other suitable communication protocol or medium. Additionally, third party systems and databases can be operably coupled to the system components via the network 430 and/or the cloud 406. For example, an EHR/EMR system (such as, the system 408) can be operably coupled to the cloud 406 to transmit patient information, scheduling information relating to a surgery, surgeon information, or any other relevant information to perform remote surgery.

The data transmitted to and from the components of system 400, can include any format, including JavaScript Object Notation (JSON), transfer control protocol (TCP)/IP, extensible markup language (XML), hypertext markup language (HTML), American Standard Code for Information Interchange (ASCII), short message service (SMS), comma-separated value (CSV), representational state transfer (REST), or other suitable format. The data transmission can include a message, flag, header, header properties, metadata, and/or a body, or be encapsulated and packetized by any suitable format having same.

The network 430 and/or the cloud 406, including the orchestration application 432, connectivity server 434, adapter management system 436, and data and analytics platform 438, can be implemented in hardware, software, or a suitable combination of hardware and software therefor, and may comprise one or more software systems operating on one or more servers having one or more processors with access to memory. The network 430 and/or the cloud 406, including the orchestration application 432, connectivity server 434, adapter management system 436, and data and analytics platform 438, can include electronic storage, one or more processors, and/or other components. The network 430 and/or the cloud 406, including the orchestration application 432, connectivity server 434, adapter management system 436, and data and analytics platform 438, can include communication lines, connections, and/or ports to enable the exchange of information via a network 430 and/or the cloud 406, and/or other computing platforms. The network 430 and/or the cloud 406, including the orchestration application 432, connectivity server 434, adapter management system 436, and data and analytics platform 438, can also include a plurality of hardware, software, and/or firmware components operating together to provide the functionality attributed herein. For example, the network 430 can be implemented by a cloud of computing platforms operating together as the network 430, including Software-as-a-Service (SaaS) and Platform-as-a-Service (PaaS) functionality. Additionally, the cloud 406 can be implemented using commercial cloud computing platforms, including all such functionality provided by the commercial cloud computing platform.

Any of the components of the system 400 can comprise electronic storage that stores information. The electronic storage can include one or both of system storage that can be provided integrally (such as, substantially non-removable) with the network 430 and/or the cloud 406, and/or removable storage that can be removably connectable to the network 430 and/or the cloud 406 via, for example, a port (such as, a Universal Serial Bus (USB) port, a firewire port, etc.) or a drive (such as, a disk drive, etc.). Electronic storage may include one or more of optically readable storage media (such as, optical disks, etc.), magnetically readable storage media (such as, magnetic tape, magnetic hard drive, floppy drive, etc.), electrical charge-based storage media (such as, erasable electronic programmable read only memory (EEPROM), random access memory (RAM), etc.), solid-state storage media (such as, flash drive, etc.), and/or other electronically readable storage media. Electronic storage may include one or more virtual storage resources (such as, cloud storage, a virtual private network, and/or other virtual storage resources). The electronic storage can include a database, or public or private distributed ledger (such as, blockchain). Electronic storage can store machine-readable instructions, software algorithms, control logic, data generated by processor(s), data received from server(s), data received from computing platform(s), and/or other data that can enable server(s) to function as described herein. The electronic storage can also include third-party databases accessible via the network 430 and/or the cloud 406.

Any of the components of the system 400 can include control circuitry, such as processor(s) or controller(s), configured to provide data processing capabilities, for instance, in the network 430 and/or the cloud 406. As such, any of the processors can include one or more of a digital processor, an analog processor, a digital circuit designed to process information, an analog circuit designed to process information, a state machine, and/or other mechanisms for electronically processing information, such as field programmable gate arrays (FPGAs) or application specific integrated circuits (ASICs). The processor(s) can be a single entity or include a plurality of processing units. These processing units can be physically located within the same device, or processor(s) can represent processing functionality of a plurality of devices or software functionality operating alone, or in concert. A networked computer processor can be a processor operably coupled to the network 430 and/or the cloud 406. The networked computer processor can be operably coupled to other processors, databases, or components.

The orchestration application 432, connectivity server 434, adapter management system 436, and data and analytics platform 438 can be configured with machine-readable instructions having one or more functional modules. The machine-readable instructions can be implemented on one or more servers, having one or more processors, with access to memory. The machine-readable instructions can be a single networked node, or a machine cluster, which can include a distributed architecture of a plurality of networked nodes. The machine-readable instructions can include control logic for implementing various functionality, as described in more detail below. The machine-readable instructions can include certain functionality associated with the system 400. Additionally, the machine-readable instructions can include a smart contract or multi-signature contract that can process, read, and write data to the database, distributed ledger, or blockchain.

Figure 5:
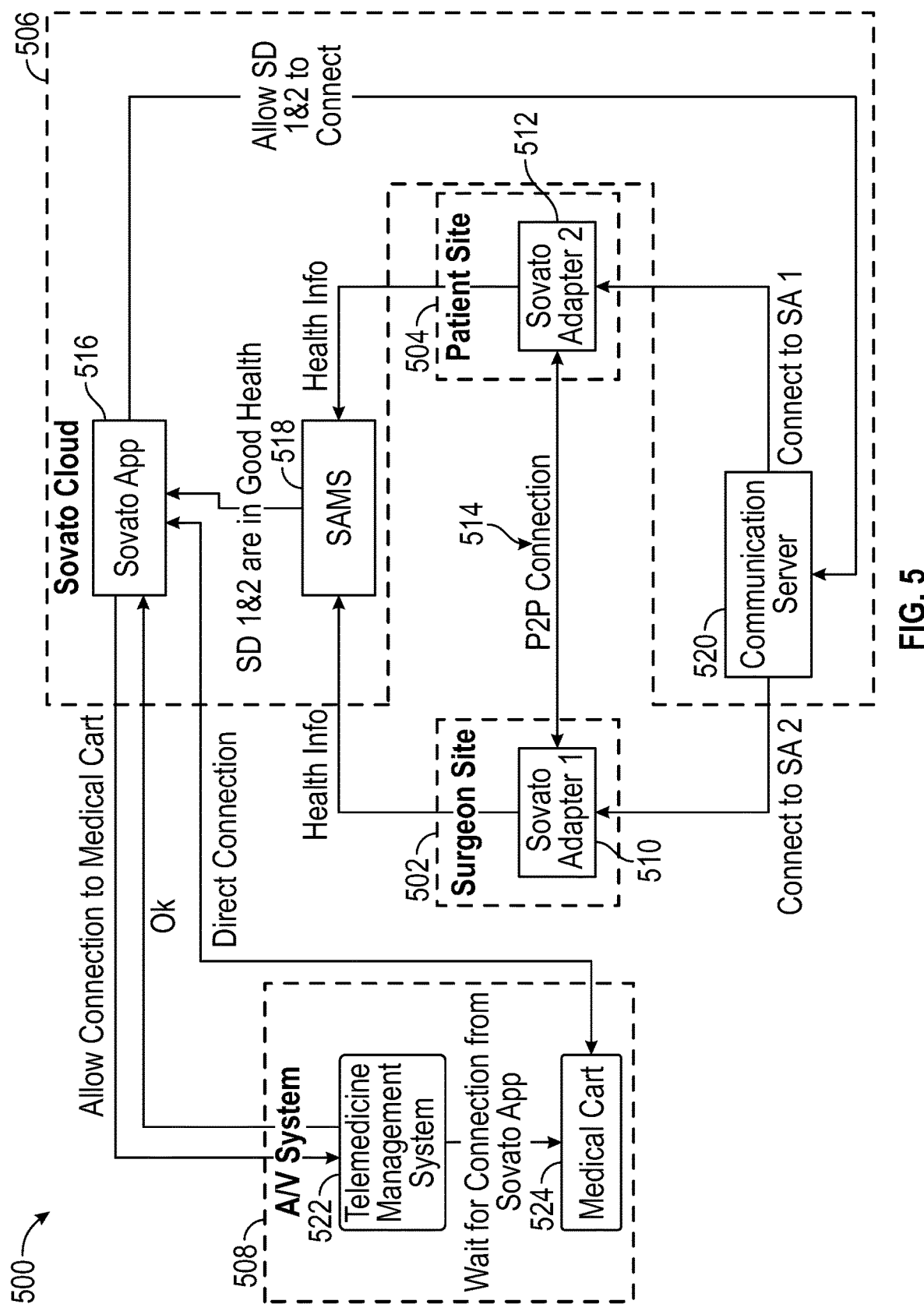
FIG. 5 is a schematic view of a remote surgery system.

Referring to FIG. 5, illustrates a schematic view of a remote surgery system 500. The system 500 can be same as or similar to the system 400. The system 500 can include one or more surgeon sites 502 having one or more adapters 510. The system 500 can include one or more patient sites 504 having one or more adapters 512. The system 500 can include a cloud 506, including an orchestration application 516, a connectivity server 520, and an adapter management system 518. The system 500 can include an A/V system 508 including a third-party telemedicine hardware management system 522 and medical cart 524. The system 500 illustrates that a connection 514 (which can be peer-to-peer) has been established between the surgeon-side adapter 510 and the patient-side adapter 512. Such connection can be established using any of the approaches described herein.

Heterogeneous and Homogenous Configurations

Figures 1, 6A:
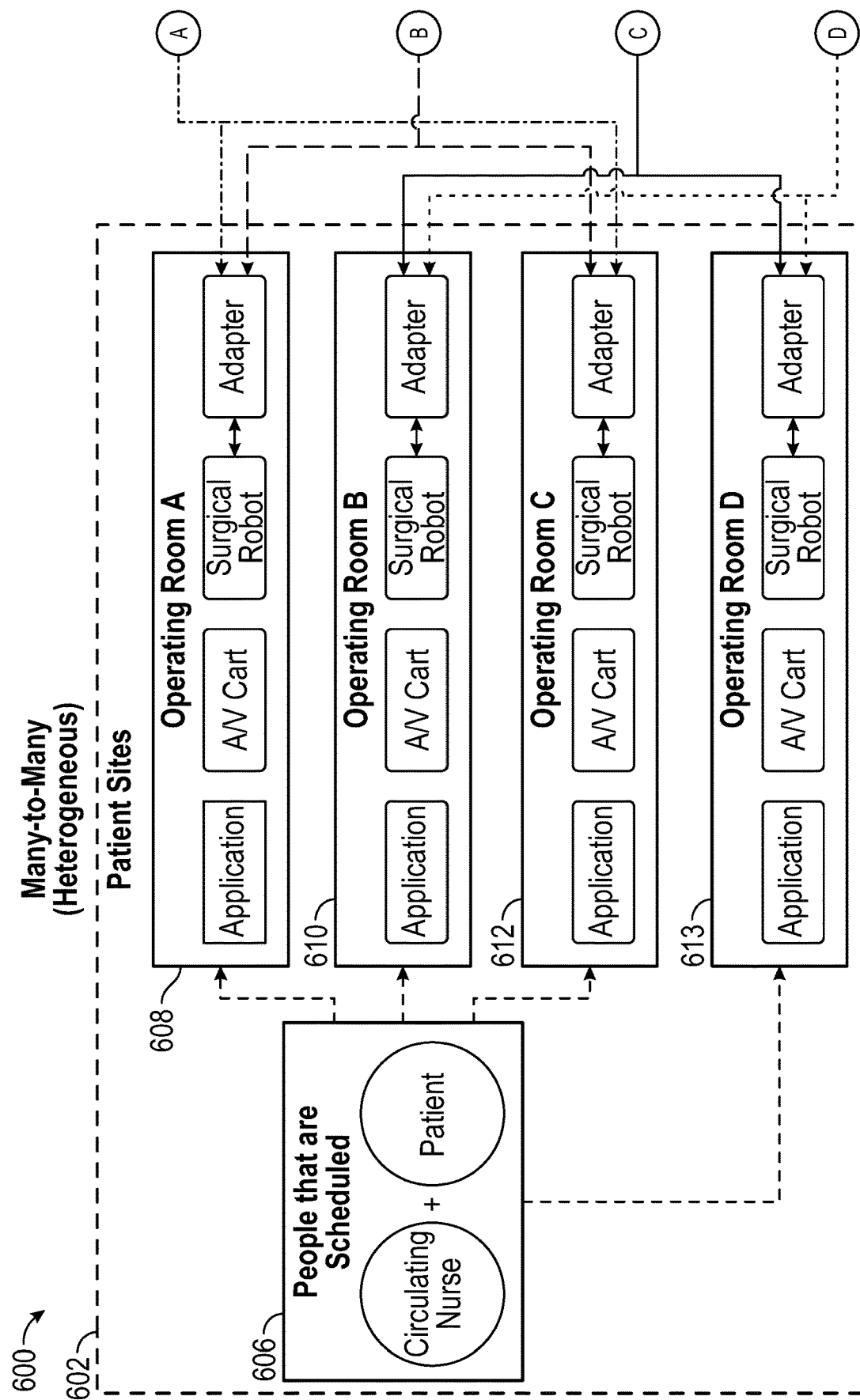
Figures 2, 6A:
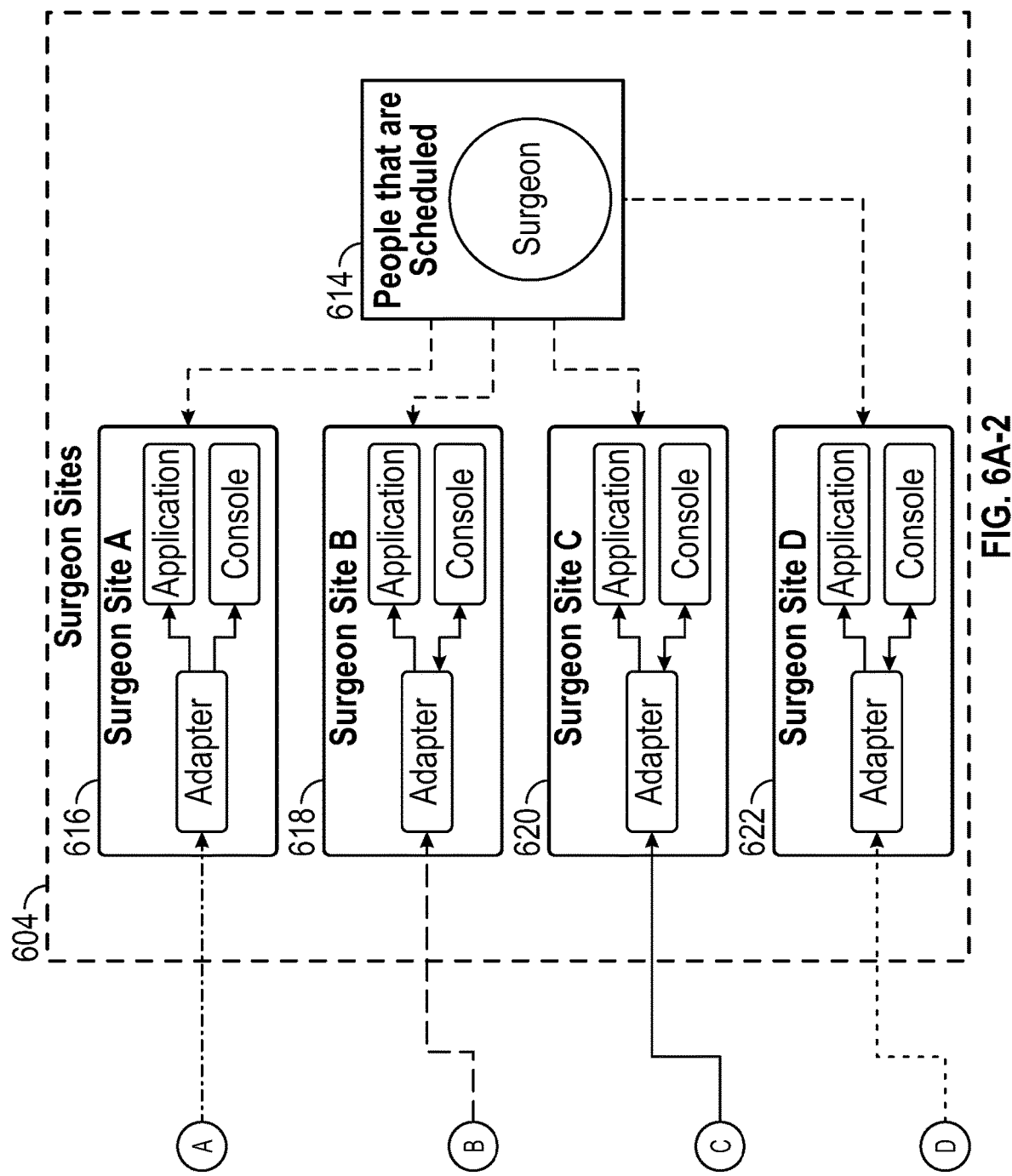

FIG. 6A-1 and FIG. 6A-2 (collectively referred to herein as FIG. 6A) illustrates a schematic view of a remote surgery system 600 configured to provide remote surgery to many patients from many surgeons. In some instances, the system 600 can include different types of surgeon consoles and surgical robots and may be referred to as "many-to-many" or heterogenous system. The system 600 can include a plurality of patient sites 602 having one or more personnel 606 and patient sites or operating rooms 608, 610, 612, 613. The system 600 can further include a plurality of surgeon sites 604 having one or more surgeons 614 and one or more surgeon locations or sites 616, 618, 620, 622.

In the patient sites 602, the one or more personnel 606 can be individuals who are scheduling and assisting the surgical operations for patients. For example, the individual scheduling the surgery may be a circulating nurse, who may enter a notification of a scheduled operation into multiple web-based interfaces, such as the nurse's interface and a remote robotic surgery scheduling application. In another example, the individual scheduling the surgery may enter a notification of a scheduled operation into a single web-based interface (such as, the EHR interface), which may include an API for the remote robotic surgery scheduling application to streamline scheduling of operations. In another example, the individual scheduling the surgery may obtain scheduling data from a hospital scheduling service, and provide the scheduling information directly to the remote robotic surgery scheduling application, without the nurse (or another person) entering scheduling information. The one or more personnel 606 can include individuals associated with the operating rooms 608, 610, 612, 613. For example, the one or more personnel 606 can include a circulating nurse, who provides care to one or more patients scheduled to receive surgery in one of the operating rooms 608, 610, 612, 613.

The operating rooms 608, 610, 612, 613 can include locations where the patient will have surgery performed. Each of the operating rooms 608, 610, 612, 613 can include a remote robotic surgery application, A/V cart, a surgical robot, and an adapter.

In an example, the remote robotic surgery application can include any or all of the programs executing on the nurse PC 420. For example, the remote robotic surgery application can interface with the orchestration application 432 executing as part of the cloud 406. The remote robotic surgery application can interface with the orchestration application 432 via a web browser.

In an example, the A/V cart can include the medical-grade A/V system 410 and the telemedicine device 428 of FIG. 4. For example, the A/V cart can be configured to transmit real-time video and audio footage of one of the operating rooms 608, 610, 612, 613 to at least one of the one or more surgeon sites 616, 618, 620, 622. The system 600 can include each of the operating rooms 608, 610, 612, 613 providing audio and video footage to more than one of the one or more surgeon sites 616, 618, 620, 622.

In an example, the surgical robot can be same as or similar to the surgical robot 422 of FIG. 4. The surgical robot can be of a specific type. For example, the type can include one or more of a manufacturer, model, or software/firmware of the surgical robot.

In an example, the adapter can be same as or similar to the patient-side adapter 426 of FIG. 4. The adapter can provide remote robotic surgery abilities to various types of surgical robots. The system 600 can include each of the operating rooms 608, 610, 612, 613 providing information transmitted by the respective adapter to more than one of the one or more surgeon sites 616, 618, 620, 622.

The surgeon sites 604 can correspond to locations where one or more surgeons are scheduled to perform remote robotic surgery.

The one or more surgeons 614 are surgeons scheduled to perform surgery on at least one patient scheduled or assisted by one or more personnel 606.

The one or more surgeon sites 616, 618, 620, 622 can include locations where the surgeon will perform remote robotic surgery. Each of the one or more surgeon sites 616, 618, 620, 622 can include a remote robotic surgery application, a surgical robot console, and an adapter.

In an example, the remote robotic surgery application can include any or all of the programs executing on the surgeon PC 412. For example, the remote robotic surgery application can interface with the orchestration application 432 executing as part of the cloud 406.

In an example, the surgical robot console can be same as or similar to the surgeon input console 416 of FIG. 4. The surgical robot console can be of a specific type. For example, the type can include one or more of a manufacturer, model, or software/firmware of the surgical robot console. In the many-to-many configuration, certain surgical robot consoles at the surgeon sites 616, 618, 620, 622 can be compatible with certain surgical robots in the operating rooms 608, 610, 612, 613. The many-to-many configuration would include incompatible surgical robot consoles and surgical robots. For example, surgical robot consoles at the surgeon sites 616 and 618 can be compatible with the surgical robots in the operating rooms 608 and 612, but not with the surgical robots in the operating rooms 610 and 613. As another example, surgical robot consoles at the surgeon sites 620 and 622 can be compatible with the surgical robots in the operating rooms 610 and 613, but not with the surgical robots in the operating rooms 608 and 612.

In an example, the adapter can be same as or similar to the surgeon-side adapter 418 of FIG. 4. The adapter can provide remote robotic surgery control abilities to various types of surgical robots. The many-to-many configuration of the system 600 can include each of the one or more surgeon sites 616, 618, 620, 622 providing information transmitted by the adapter to any of the operating rooms 608, 610, 612, 613.

In some implementations, the system 600 is configured to create surgical sessions. Such sessions may comprise information describing allotted time slots, surgical team information, patient-side surgical system requirements, and surgeon-side console requirements. An allotted time slot may comprise an estimation of the amount of time a procedure is likely to take and the date and time the procedure is to begin. Surgical team information may comprise the names of medical staff (which can include one or more of the personnel 606) assigned to a procedure and their professional medical roles during a procedure. Patient-side surgical requirements may comprise requirements for one or more robotic arms, one or more imaging systems, and the type of patient-side robotic system. Surgeon-side console requirements may comprise descriptions of display system capabilities, input devices, audio-visual communication systems, and type of surgeon-side console. The type of patient-side robotic system can comprise information describing one or more of the brand, model, or software/firmware of robotic system which must match the type of surgeon-side console. The type of surgeon-side console can comprise information describing one or more of the brand, model, or software/firmware of surgeon console compatible with the patient-side robotic system.

Figure 6B:
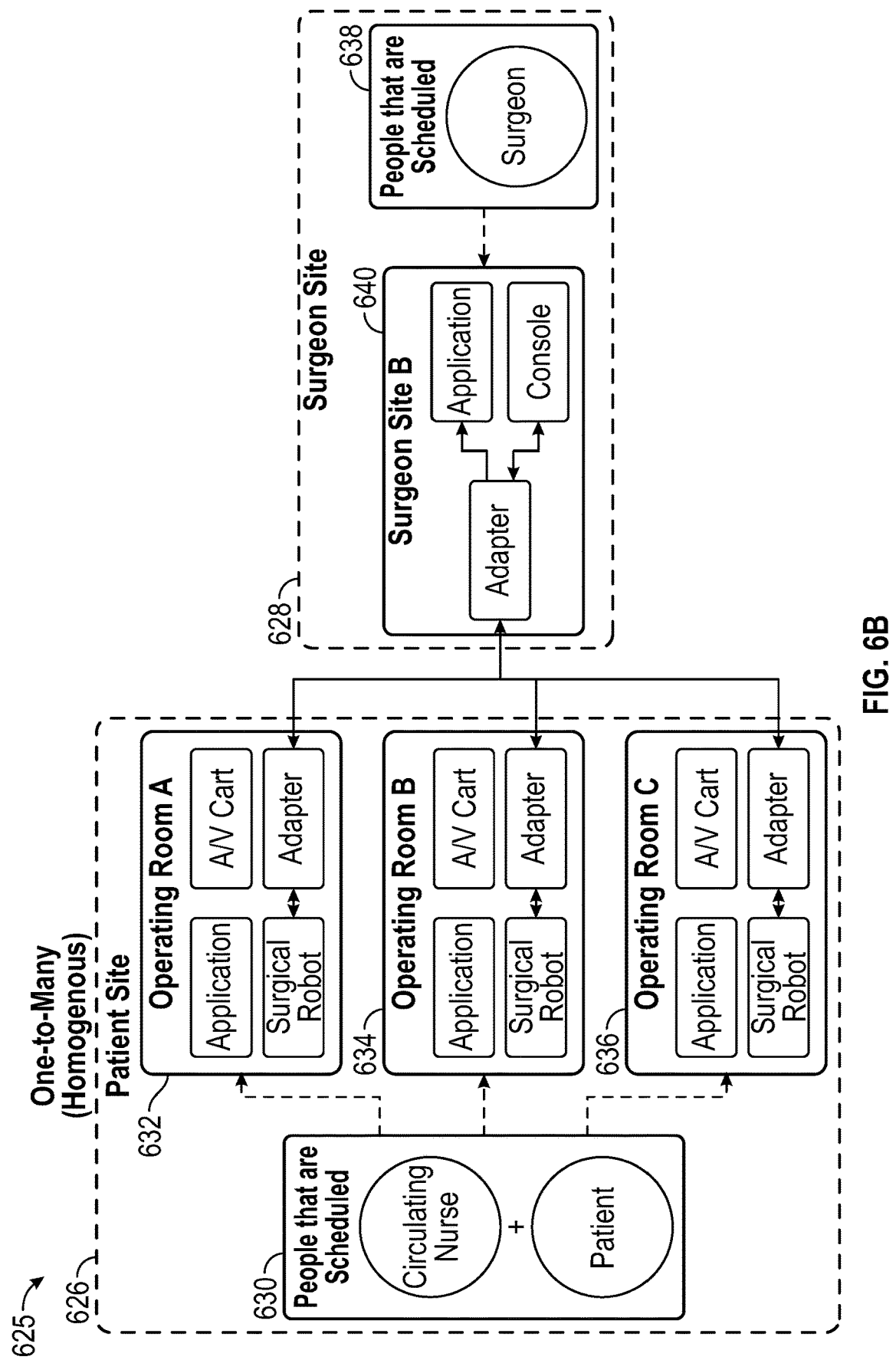

FIG. 6B illustrates a schematic view of a remote surgery system 625 configured to provide remote surgery to many patients from one remote surgery location. In some instances, the system 625 can be referred to as "one-to-many." In such one-to-many configuration, multiple surgical robots can be remotely controlled from a surgical robot console, which is of the same type as each of the surgical robots. That is, the system 625 may only include homogenous devices. For example, a surgical robot console 640 of a surgeon site 628 is the same type as the surgical robots in operating rooms 632, 634, 636. In the example system 625, there is one console in the surgeon site 628 that can connect to and control many surgical robots of same type. For example, the surgeon site 628 can control the connected components of the operating rooms 632, 634, 636.

The system 625 can include a plurality of patient sites 626 having one or more personnel 630 and operating rooms 632, 634, 636. The system 625 can further include a surgeon site 628 having a surgeon 638 and one surgeon site 628. While the system 625 is similar to the system 600 of FIG. 6A, the system 625 illustrates an example of one remote surgery location (namely, the surgeon site 628) controlling surgery in multiple patient locations.

Similar to the patient sites 602 in FIG. 6A, the patient sites 626 can correspond to locations where one or more patients are scheduled to have surgery performed.

Similar to the one or more personnel 606 in FIG. 6A, the one or more personnel 630 can be individuals who are scheduling and assisting the surgical operations for the patients.

The operating rooms 632, 634, 636 can include locations where the patient will have surgery performed. As described in connection with FIG. 6A, each of the operating rooms 632, 634, 636 can include a remote robotic surgery application, A/V cart, a surgical robot, and an adapter.

As described in connection with FIG. 6A, in an example, the remote robotic surgery application can include any or all of the programs executing on the nurse PC 420. For example, the remote robotic surgery application can interface with the orchestration application 432 executing as part of the cloud 406.

As described in connection with FIG. 6A, in an example, the A/V cart can include the medical-grade A/V system 410 and the telemedicine device 428 of FIG. 4. For example, the A/V cart can be configured to transmit real-time video and audio footage of one of the operating rooms 632, 634, 636 to the surgeon site 628. The one-to-many configuration of the system 625 can include each of the operating rooms 632, 634, 636 providing audio and video footage to the surgeon site 628.

As described in connection with FIG. 6A, in an example, the surgical robot can be same as or similar to the surgical robot 422 of FIG. 4. The surgical robot can be of a specific type. For example, the type can include one or more of a manufacturer, model, or software/firmware of the surgical robot.

As described in connection with FIG. 6A, in an example, the adapter can be same as or similar to the patient-side adapter 426 of FIG. 4. The adapter can provide remote robotic surgery abilities to various types of surgical robots. The one-to-many configuration of the system 625 can include each of the operating rooms 632, 634, 636 providing information transmitted by the respective adapter to the surgeon site 628.

The surgeon site 628 can include the surgical console 640 where one or more surgeons 638 are scheduled to perform remote robotic surgery.

The one or more surgeons 638 can perform surgery on at least one patient being scheduled or assisted by the one or more personnel 630.

As described in connection with FIG. 6A, the surgeon site 628 can include a location where a surgeon will perform remote robotic surgery. The surgeon site 628 can include a remote robotic surgery application, a surgical robot console, and an adapter.

In an example, the remote robotic surgery application can include any or all of the programs executing on the surgeon PC 412. For example, the remote robotic surgery application can interface with the orchestration application 432 executing as part of the cloud 406.

In an example, the surgical robot console can be same as or similar to the surgeon input console 416 of FIG. 4. The surgical robot console can be of a specific type. For example, the type can include one or more of a manufacturer, model, or software/firmware of the surgical robot console.

In an example, the adapter can be same as or similar to the surgeon-side adapter 418 of FIG. 4. The adapter can provide remote robotic surgery control abilities to various types of surgical robots. The one-to-many configuration of the system 625 can include the surgeon site 628 providing information transmitted by the adapter to one or more of the operating rooms 632, 634, 636.

As is described in connection with FIG. 6A, the system 625 is configured to create surgical sessions.

Figure 6C:
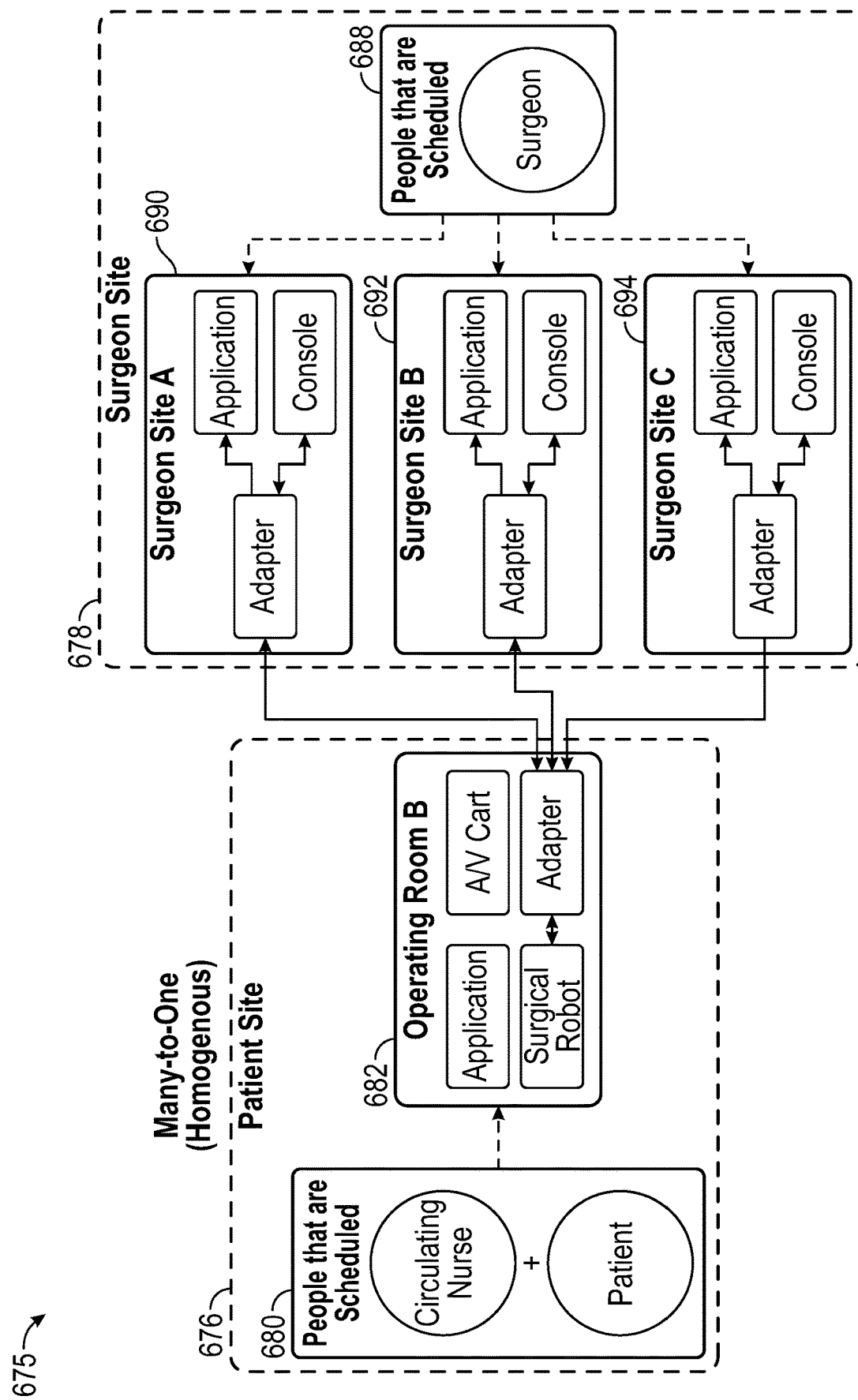

FIG. 6C illustrates a schematic view of a remote surgery system 675 configured to provide remote surgery to one patient from many surgeons. In some instances, the system 675 can be referred to as "many-to-one." In such many-to-one configuration, a surgical robot can be remotely controlled from multiple surgical robot consoles. That is, surgical robot consoles of surgeon sites 690, 692, 694 are the same type as a surgical robot in an operating room 682. In the example systems 675, there is one console in each of the surgeon sites 690, 692, 694 that can connect to and control one surgical robot of the same type. For example, the surgeon sites 690, 692, 694 can control the connected components of the operating room 682.

The system 675 can include a plurality of patient sites 676 having one or more personnel 680 and an operating room 682. The system 675 can further include a plurality of surgeon sites 678 having one or more surgeons 688 and one or more surgeon sites 690, 692, 694. While the system 675 is similar to the system 600 of FIG. 6A, the system 675 illustrates an example of multiple remote surgery locations controlling surgery in one patient location (namely, the operating room 682).

Similar to the patient sites 602 in FIG. 6A, the patient sites 676 can correspond to locations where one or more patients are scheduled to have surgery performed.

Similar to the one or more personnel 606 in FIG. 6A, the one or more personnel 680 can be individuals who are scheduling and assisting the surgical operations for the patients.

The operating room 682 can include a location where the patient will have surgery performed. As described in connection with FIG. 6A, the operating room 682 can include a remote robotic surgery application, A/V cart, a surgical robot, and an adapter.

As described in connection with FIG. 6A, in an example, the remote robotic surgery application can include any or all of the programs executing on the nurse PC 420. For example, the remote robotic surgery application can interface with the orchestration application 432 executing as part of the cloud 406.

As described in connection with FIG. 6A, in an example, the A/V cart can include the medical-grade A/V system 410 and the telemedicine device 428 of FIG. 4. For example, the A/V cart can be configured to transmit real-time video and audio footage of the operating room 682 to at least one of the one or more surgeon sites 690, 692, 694. The many-to-one configuration of the system 675 can include the operating room 682 providing audio and video footage to more than one of the one or more surgeon sites 690, 692, 694.

As described in connection with FIG. 6A, in an example, the surgical robot can be same as or similar to the surgical robot 422 of FIG. 4. The surgical robot can be of a specific type. For example, the type can include one or more of a manufacturer, model, or software/firmware of the surgical robot.

As described in connection with FIG. 6A, in an example, the adapter can include the patient-side adapter 426 of FIG. 4. The adapter can provide remote robotic surgery abilities to various types of surgical robots. The many-to-one configuration of the system 675 can include the operating room 682 providing information transmitted by the adapter to more than one of the one or more surgeon sites 690, 692, 694.

The surgeon sites 678 can include multiple locations or sites 690, 692, 694 where one or more surgeons 688 are scheduled to perform remote robotic surgery.

The one or more surgeons 688 can perform surgery on at least one patient being scheduled or assisted by the one or more personnel 680.

As described in connection with FIG. 6A, the one or more surgeon sites 690, 692, 694 can include locations where the surgeon will perform remote robotic surgery. Each of the one or more surgeon sites 690, 692, 694 can include a remote robotic surgery application, a surgical robot console, and an adapter.

In an example, the remote robotic surgery application can include any or all of the programs executing on the surgeon PC 412. For example, the remote robotic surgery application can interface with the orchestration application 432 executing as part of the cloud 406.

In an example, the surgical robot console can be same as or similar to the 416 416 of FIG. 4. The surgical robot console can be of a specific type. For example, the type can include one or more of a manufacturer, model, or software/firmware of the surgical robot console.

In an example, the adapter can be same as or similar to the surgeon-side adapter 418 of FIG. 4. The adapter can provide remote robotic surgery control abilities to various types of surgical robots. The many-to-one configuration of the system 675 can include each of the one or more surgeon sites 690, 692, 694 providing information transmitted by the respective adapter to the operating room 682.

As is described in connection with FIG. 6A, in some implementations, the system 675 is configured to create surgical sessions.

Figure 7:
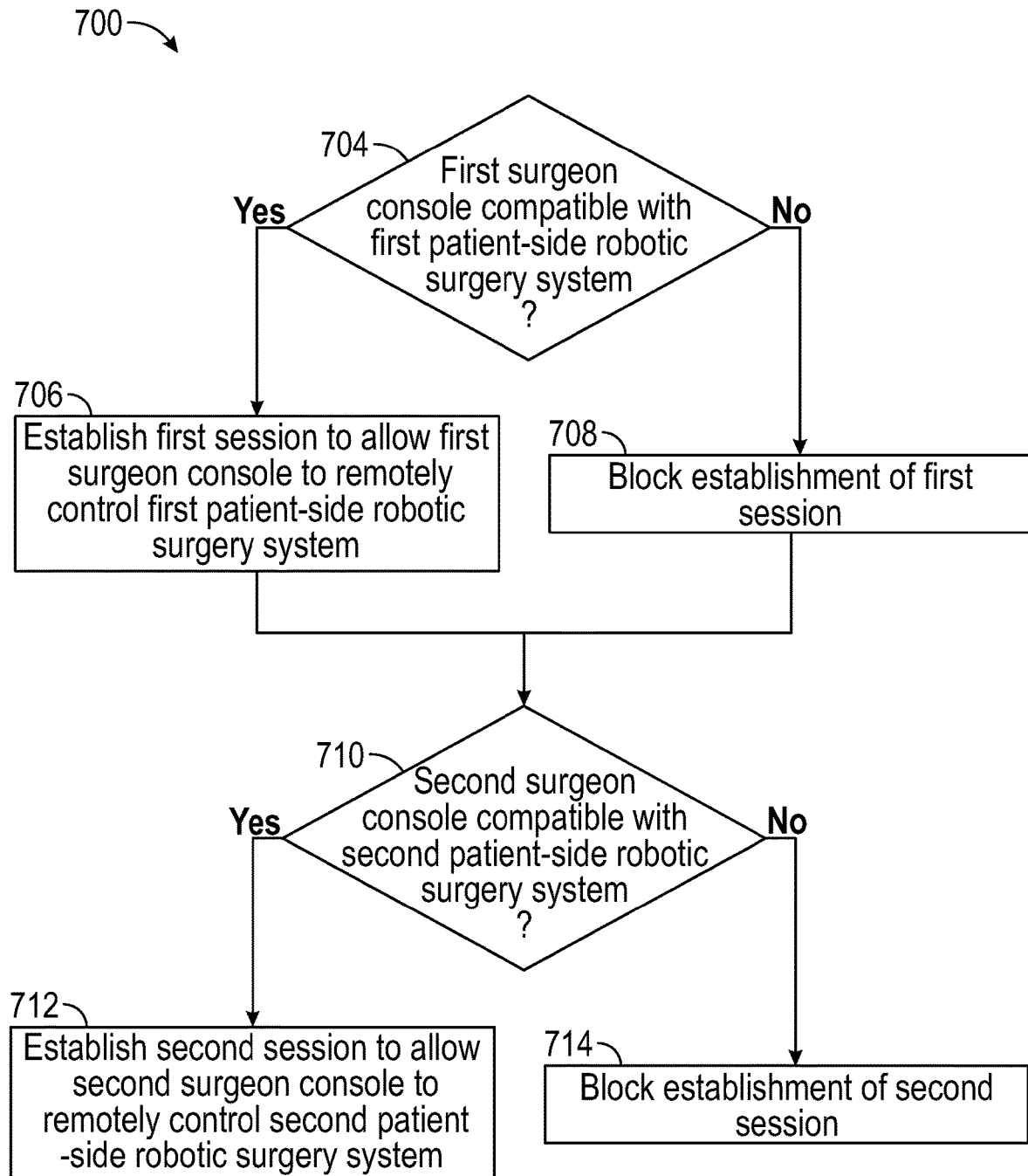
FIG. 7 is a block diagram of a process of remotely controlling surgical procedures.

FIG. 7 illustrates a process 700 of remotely controlling surgical procedures. The process 700 can be implemented by a system for remotely controlling robotic surgery, such as the system 600. In some examples, the orchestration application 432, can implement the blocks or steps of the process 700.

At block or step 704, the process 700 can verify whether a first surgeon console is compatible with a first patient-side robotic surgery system. As described herein, this can entail verifying that the first surgeon console and the first patient-side robotic surgery system are of the same type, such the first type. For instance, the process 700 can compare the type of the first surgeon console with the type of the first patient-side robotic surgery system to determine if the types match. The type can correspond to the manufacturer, model, and/or software/firmware of the surgeon input console (or console) or the surgical robot (or patient-side robotic surgery system). In an example, the process 700 (for instance, via the orchestration application 432) can obtain an identifier from the first surgeon-side adapter and the first patient-side adapter. In this example, the process 700 can compare the identifier with an expected identifier, depending on the type of the surgeon-side adapter and the patient-side adapter. Verification can entail determination of a match between the identifier and the expected identifier.

As described herein, the verification in step 704 can be performed well before establishing a connection for remotely controlling the first patient-side robotic surgery system (for instance, at the time a schedule is being created) and/or just before establishing the connection. In the latter case, verification can be performed in response to receiving a first request to establish a first session between a first surgeon-side adapter integrated with the first surgeon console and a first patient-side adapter integrated with the first patient-side robotic surgery system to control at least one surgical instrument and at least one imaging system of the first patient-side robotic surgery system. In the former case, verification can be performed prior to receiving the first request. The first request can be transmitted after coordination by the personnel between the patient side and surgeon side has been completed, as described herein. For example, the first request can be transmitted responsive to the surgeon completing the attestation. The first request can be transmitted by the surgeon PC 412.

Subsequent to successful verification in step 704, the process 700 can transition to step 706 where it can establish the first session to allow a first surgeon console to remotely control movement and actuation of the at least one surgical instrument and the at least one imaging system of the first patient-side robotic surgery system. As described herein, the first session can be established in response to receiving the first request, which can be transmitted well after completion of the verification or right after completion of the verification. In an example, the process 700 (for instance, via the orchestration application 432) can transmit an identifier to the surgeon-side adapter to establish the first session. For example, the process 700 can obtain an internal IP address (and, in some cases, an external IP address) of the patient-side adapter.

If the verification fails in step 704, the process 700 can transition to step 708 where it can block establishment of the first session in order to prevent the first surgeon console from remotely controlling movement and actuation of the at least one surgical instrument and the at least one imaging system of the first patient-side robotic surgery system. Verification can fail responsive to determining that there is a mismatch in the types of the first surgeon console and the first patient-side robotic surgery system. In some examples, the process 700 (such as, via the orchestration application 432) can withhold the identifier information from being transmitted to the first surgeon-side adapter, such that the first surgeon-side adapter cannot establish a session with the first patient-side adapter.

Similarly to step 704, at step 710, the process 700 can verify whether a second surgeon console with which a second surgeon-side adaptor is integrated is compatible with a second patient-side robotic surgery system. Step 710 can be performed at the same time, before, or after step 704 since steps 704 and 710 involve verifying compatibility of different sets of surgeon consoles and patient-side robotic surgery systems. For example, step 710 can be combined with step 704 (for instance, both verifications can be performed at a time of creating a schedule).

As described herein, the process 700 can receive a second request from a second surgeon-side adapter to establish a second session between the second surgeon-side adapter and a second patient-side adapter to control at least one surgical instrument and at least one imaging system of a second patient-side robotic surgery system with which the second patient-side adapter is integrated. Verification in step 710 can be performed responsive to the second request or prior to receiving the second request.

Similarly to step 706, subsequent to a successful verification in step 710, the process 700 can transition to step 712 where it can establish the second session to allow the second surgeon console to remotely control movement and actuation of the at least one surgical instrument and the at least one imaging system of the second patient-side robotic surgery system.

As described herein in connection with the step 704, if the verification fails in step 710, the process 700 can transition to step 714 where it can block establishment of the second session to prevent the second surgeon console from remotely controlling movement and actuation of the at least one surgical instrument and the at least one imaging system of the second patient-side robotic surgery system.

The process 700 can establish the first session by transmitting an IP address of the first patient-side adapter to the first surgeon-side adapter so that the first patient-side adapter and the first surgeon-side adapter can establish a connection. After receiving the internal IP address (and, in some cases, the external IP address) of the patient-side adapter, the surgeon-side adapter can direct network communications directly to the IP address of the first patient-side adapter, thereby establishing the connection. The process 700 can similarly establish the second session.

The process 700 can provide a connectivity service to the first patient-side adapter and the first surgeon-side adapter to establish a connection (which can be a peer-to-peer connection), as described herein. The process 700 can similarly treat the second request and similarly establish the second session.

The process 700 can provide an adapter management service to the first patient-side adapter and the first surgeon-side adapter to establish a connection. The first request can include a query for an internal IP address (and, in some cases, the external IP address) of the first patient-side adapter. The process 700 can similarly treat the second request and similarly establish the second session.

Planning Surgical Sessions

Figure 8:
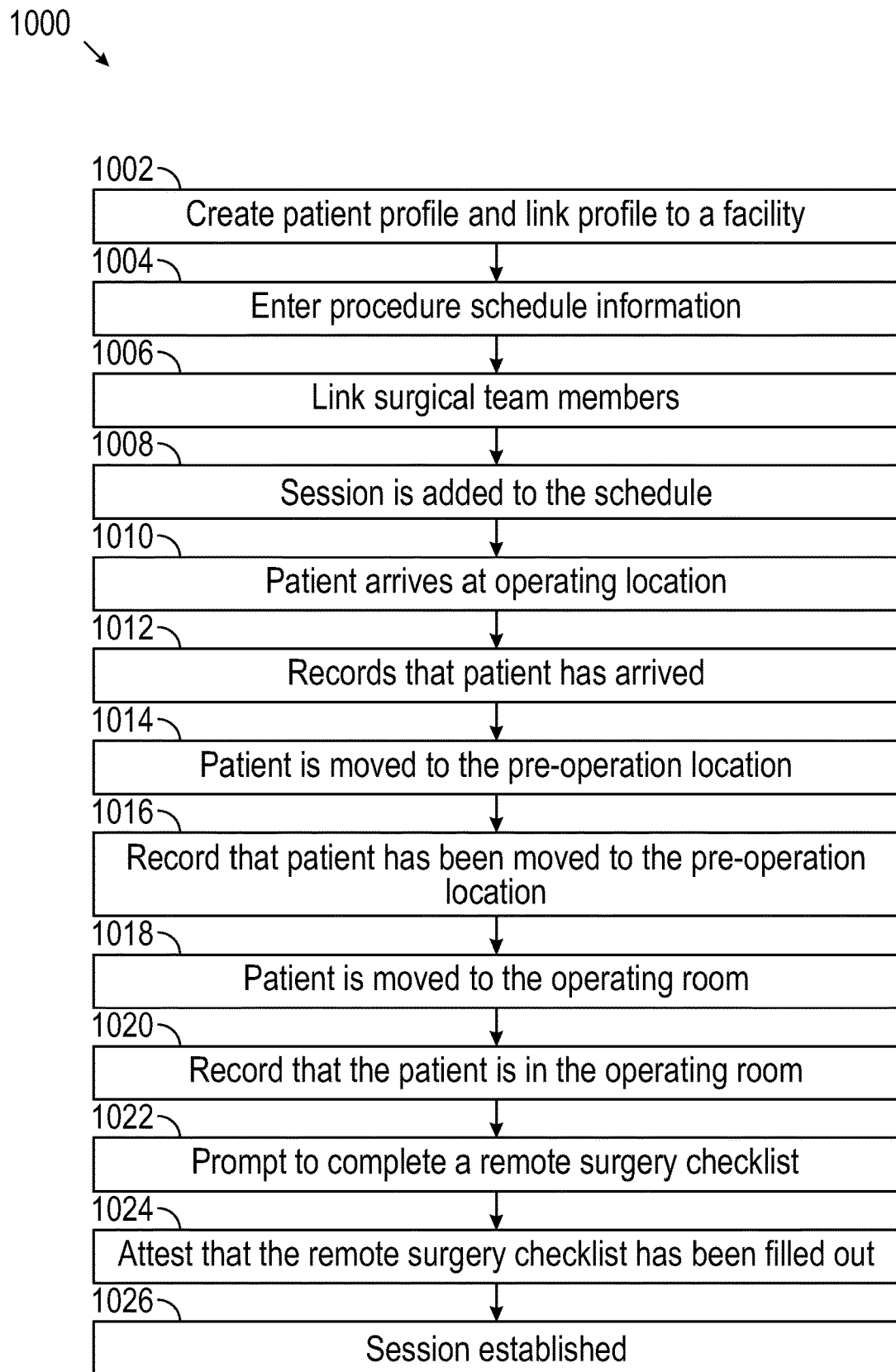
FIG. 8 is a block diagram of a process for planning and establishing surgical sessions.

FIG. 8 illustrates a flow chart of a process 1000 for planning (or scheduling) and establishing surgical sessions (or sessions) for remotely controlling a patient-side surgical system. The process 1000 can be implemented by any of the remote surgery systems described herein, such as the system 400, 600, 625, or 675. In some cases, the process 1000 can be implemented by the orchestration application 432.

A remote surgery coordinator (RSC) or another user can schedule a session, such as via a computing device in communication with the orchestration application 432. Such computing device may be located anywhere (and not necessarily patient side or surgeon side) and can be connected to the orchestration application 432 via the network 430. The process 1000 can start at block or step 1002, where the RSC creates a patient profile, which can include patient identification information, patient's health information, or the like. Patient's health information may include one or more of a patient's list of current medications, past medications, immunizations, current treatments, past treatments, and notes from medical professionals.

At step 1004, the RSC can schedule a session for remotely operating on the patient (whose profile had been created at step 1002). Schedule information entered at step 1004 can include one or more of: surgery type, identification of the patient, identification of a surgeon, surgical team information, operating room team information, patient-side surgical system requirements, and surgeon-side console requirements, allotted session time slot, and the physical location of the surgical facility at which the surgical procedure will take place. As described herein in connection with FIG. 6A, the allotted session time slot may comprise an estimation of the amount of time the surgical procedure is likely to take and the date and time the surgical procedure is to begin. In some instances, the allotted session time slot can be scheduled to be longer than the anticipated time for the surgeon to complete the surgical procedure. For example, if the anticipated time to complete the surgery procedure is 30 minutes, the estimation of the amount of time the surgical procedure is likely to take may be 30 minutes to provide sufficient time for 1) pre-op work by medical staff to prepare a patient for the surgical procedure (during this time the surgeon may be able to communicate with the medical staff over A/V), 2) the surgeon to perform the surgical procedure, and 3) post-op work by the medical staff after the surgeon has completed the surgical procedure. Each of these three tasks may take 30 minutes. Surgical team information may comprise the names of medical staff assigned to the surgical procedure and their professional medical roles during the surgical procedure. Patient-side surgical requirements may comprise requirements for one or more robotic arms, one or more imaging systems, and the type of patient-side robotic system. Surgeon-side console requirements may comprise descriptions of display system capabilities, input devices, audio-visual communication systems, and type of surgeon-side console. The type of patient-side robotic system comprises information describing one or more of the brand, model, or software/firmware of robotic system which must match the type of surgeon-side console. The type of surgeon-side console comprises information describing one or more of the brand, model, or software/firmware of surgeon console compatible with the patient-side robotic system. Schedule information can also include surgeon-side and/or patient-side adapter identification information, which may include the adapter's IP address (such as, the internal IP address) and/or serial number.

In some examples, the allotted session time slot can be modified after the session has been scheduled. For example, a modification can be made responsive to start time of surgery having been delayed or surgery taking longer duration than originally scheduled duration of time. In this manner, a surgeon can be allowed to remotely control surgery in a time slot different than the originally scheduled allotted session time slot. Modifications to the allotted session time slot can be made by the RSC.

In some cases, at least some of the schedule information can be generated by the health system information system 408 and may be entered into the orchestration application by the RSC in step 1004. The health information system 408 may be a third-party electronic health record system such as Epic®, Erner®, or another company.

In some instances, the schedule information can be transmitted to the orchestration application 432 by the health system information system 408, without being entered by the RSC.

Figure 9B:
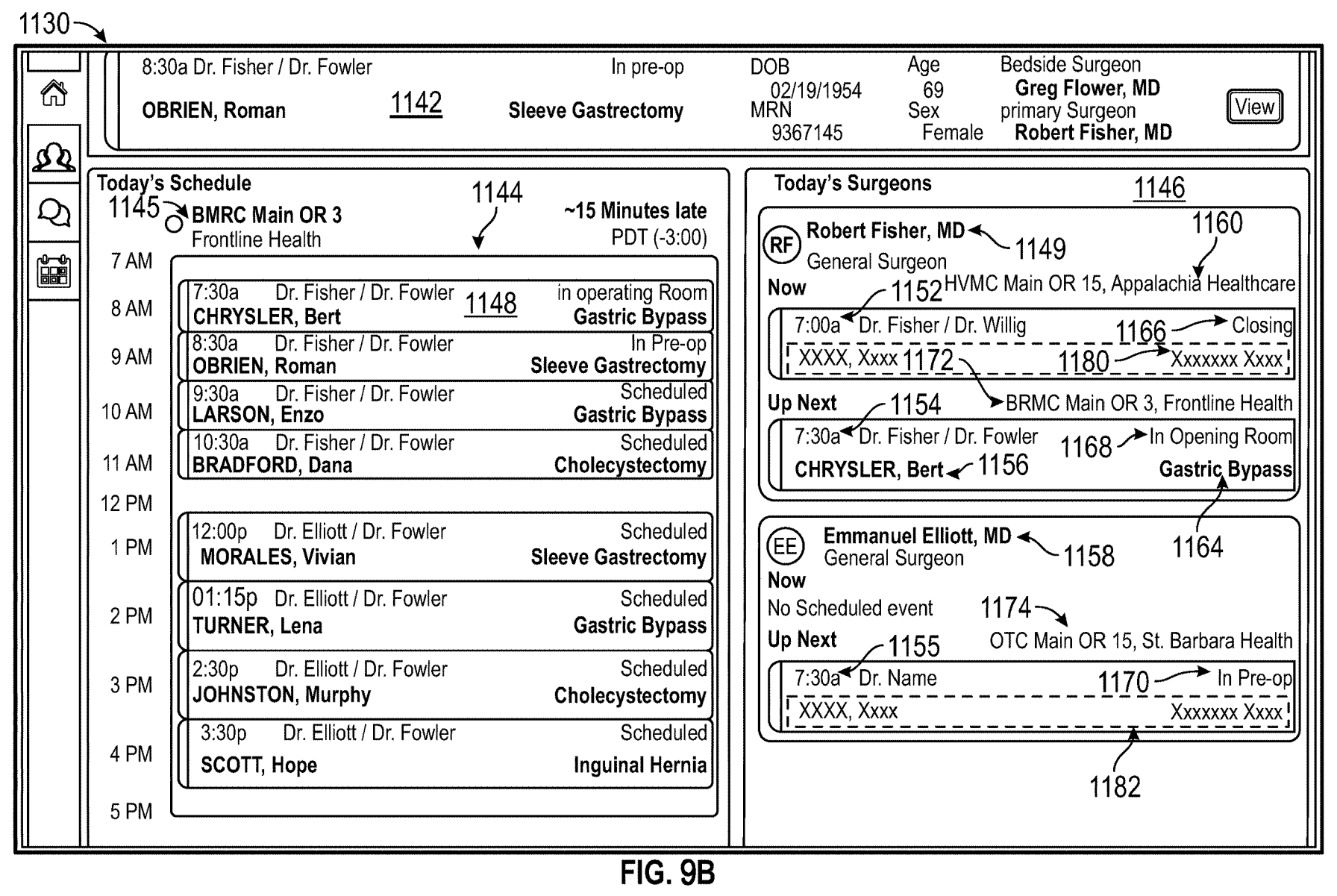

The process 1000 can transition to step 1006 where it can link surgical team members to the surgical procedure. Linking surgical team members to the surgical procedure can include selecting medical professionals that will participate in the surgical procedure, such as one or more surgeons who will perform the surgical procedure and the operating room staff comprised of nurses and support staff. After the RSC links surgical team members to the is surgical procedure, a corresponding scheduled surgical session can be added to the schedule at step 1008. The schedule can be maintained by the process 1000, such as by the orchestration application 432. As described herein and illustrated in FIGS. 9A and 9B, the scheduled surgical session can be displayed on the monitor 414 connected to the surgeon PC 412 and/or nurse PC 420 in a list of time-ordered scheduled surgical session entries (or otherwise output to a surgeon and support staff). Such displaying (or otherwise outputting) the list (as shown in FIGS. 9A and 9B) can facilitate the subsequent steps of preparing for and performing a remotely controlled surgical procedure.

The process 1000 (for instance, via the orchestration application 432) may be configured to transmit scheduled surgical session information to one or more surgeon-side PCs 412 for output (such as, on the monitor 414). In this example, when one or more scheduled surgical sessions are created at step 1008, such one or more scheduled surgical sessions may be associated with one or more surgeons and surgical sessions information would be transmitted to one or more surgeon-side PCs 412 of such one or more surgeons. In some examples, the process 1000 can include a function to obtain scheduling data from the surgeon's personal calendar (e.g., Microsoft Outlook) to identify times when the surgeon is or is not available. In this manner, when a surgery is scheduled in the orchestration application, the process 1000 can include a function to insert new scheduling data onto the surgeon's personal calendar. Similarly, surgical session information can be transmitted on one or more nurse PCs 420 for output (such as, for display). Scheduled surgical sessions can be displayed as shown in FIGS. 9A and 9B.

A master schedule including scheduled surgical sessions for all surgical consoles and all patient-side surgical systems may be created by the process 1000. The master schedule can be stored by the orchestration application 432. In some instances, the steps 1002 through 1008 can be executed multiple times for different hospitals to create the master schedule. A surgeon operating at a particular location may be provided with a portion of the master schedule that includes only those scheduled surgical sessions that are scheduled to be performed by that surgeon. As illustrated in FIG. 9A, such portion (or, in the illustrated example, displayed view) of the master schedule provided to the surgeon includes scheduled surgical sessions at different operating rooms, which may be located in different hospitals. Similarly, an operating room at a particular hospital may be provided with a portion of the master that includes only those scheduled surgical sessions that are scheduled to be performed in that operating room, as explained in connection with FIG. 9B.

As described herein, compatibility of the surgeon-side console and the patient-side surgical system can be verified at step 1008 (or at step 1004 or 1006). The scheduled surgical session may not be created at step 1008 unless the types of the surgeon-side console and the patient-side surgical system match.

After the scheduled surgical session has been added to the schedule, at step 1010 the patient will arrive for the surgical procedure during the scheduled time. The patient will arrive at the surgical facility where the scheduled surgical session has been scheduled. Step 1010 can happen long after completion of step 1008, such as hours, days, or weeks later. At step 1012, the RSC records (for instance, in the orchestration application 432) that the patient has arrived at the surgical facility where the scheduled surgical session has been scheduled. After arriving at the surgical facility, the patient can be moved by surgical facility staff into a pre-operation location, as indicated at step 1014. The pre-operation location can comprise one or more rooms in which a patient may receive preparatory treatment to prepare the patient for the scheduled surgical session.

After the patient has been moved at step 1014 to the pre-operation location, at step 1016 the RSC can record (for instance, in the orchestration application 432) that the patient has been moved to the pre-operation location. The surgeon can be informed (for instance, via the orchestration application 432) that the patient has been moved to the pre-operation location.

After the pre-operation procedures are complete, the patient can be moved to an operating room at step 1018, in which a patient-side surgical system can be located. After the patient has been moved into the operating room, the RSC can record at step 1020 (such as, in the orchestration application 432) that the patient has been moved to the operating room. The surgeon can be informed that the patient is in the operating room (for instance, via the orchestration application 432).

Subsequently, at step 1022 the process 1000 can prompt that a remote surgery checklist needs to be completed. The prompt can be output (such as, displayed) on the nurse PC 420. A circulating nurse can complete the remote surgery checklist, which can include one or more of pre-operation requirements, operating room staff requirements, and patient-side surgical system requirements. The remote surgery checklist can be completed on the nurse PC 420.

After the remote surgery checklist has been completed, the process 1000 can transition to step 1024 where it can prompt the surgeon to attest the remote surgery checklist has been completed correctly. For example, the orchestration application 432 can, via the surgeon PC 412, display the attestation on the monitor 414. As described herein, completion of the checklist and attestation can be part of coordination between the remote surgeon and the operating room staff. The surgeon can attest by, for instance, clicking "Attest" on the user interface displayed on the monitor 414. The remote surgery checklist can be completed on the nurse PC 420, transmitted to the surgeon side via the network 430, displayed on the monitor 414, and attested to by the surgeon through the surgeon PC 412. Coordination can generally refer to a handshake protocol being performed between the patient side and the surgeon side to ensure that both sides are ready for execution of a remotely controlled surgical procedure. In some instances, coordination can be performed verbally using an A/V connection, as described herein. For instance, a member of the operating room staff could say "Ready" (or something similar), and the surgeon could respond "We are also ready" (or something similar).

After the surgeon has performed the attestation, a session for remotely controlling the patient-side surgical system can be initiated at step 1026. The session can be initiated responsive to a request to initiate the session, which can be transmitted by the surgeon PC 412 subsequent to completion of the attestation. For example, request to initiate the session can be transmitted responsive to the surgeon clicking "Attest" on the user interface. As described herein, in some instances, compatibility of the surgeon-side console and the patient-side surgical system can be verified (or re-verified) prior to establishing an operational connection to remotely control the patient-side robotic system. The operational connection between the patient-side surgical system and the surgeon-side console can enable the surgeon to control via the surgeon-side console movement and actuation of at least one surgical instrument and at least one imaging system of the patient-side surgical system.

The session for remotely controlling the patient-side surgical system can be associated with a time window during which a surgeon is allowed to remotely control a patient-side robotic system to operate on a patient, subsequent to a completion of coordination (such as, signoffs) as described herein. The time window can correspond to the scheduled time of the surgical session (such as, to an allotted session time slot). After such time window has opened and over duration of the time window, the operational connection from the surgeon's surgical console to remotely control the patient-side robotic system may be allowed, subsequent to the completion of coordination, while an operational connection from any other surgical console to remotely control the patient-side robotic system may be disallowed. After the time window has ended, an operational connection from the surgeon's surgical console to remotely control the patient-side robotic system may be disallowed as it is possible that another time window has been opened to permit the same or another surgical console to connect to the patient-side robotic system to remotely control the patient-side robotic system to operate on a different patient. That is, time windows for remotely controlling a particular patient-side robotic system can be arranged in non-overlapping chronological order. The operational connection may be initiated responsive to completion of the coordination between the patient side and surgeon side, which, as described herein, can involve completion of one or more checklists and attestation of the one or more checklists (this can be referred to as signoffs). The surgeon can be informed that the time window has been opened, for instance, via the surgeon PC 412 and the monitor 414 (such as, via a status being shown on a schedule, as described in connection with FIGS. 9A and 9B). In response to the notification, the surgeon can initiate the operational connection to remotely control the patient-side robotic surgery system (for instance, by clicking "Attest" on the user interface displayed on the monitor 414). On the patient side, the operating room staff can be informed that the time windows have been opened, for instance, via the nurse PC 420.

As described herein, the surgeon PC 412 and the telemedicine device 428 can establish a connection via the A/V system 410 to facilitate provision of an audio and/or video feed from the patient site 404 to the surgeon site 402 (and vice versa) as well as facilitate a two-way audio and/or video communication between the patient site 404 and the surgeon site 402. Transmission of such audio and/or video feed (which can be a two-way feed) can be permitted after the time window has been opened. In some cases, transmission of such audio and/or video feed can be permitted outside of the session for remotely controlling the patient-side surgical system (such as, before the session has been initiated or after the session has been completed) and over a time duration that exceeds the duration of the session. For example, transmission of such audio and/or video feed can be permitted prior to the initiation of the session to facilitate preparation of the patient for the surgical procedure (such as, facilitate pre-surgical preparation) and complete the coordination between a surgeon and patient-side staff. As another example, transmission of such audio and/or video feed can be permitted after the closing of the session window to facilitate completion of the surgical procedure (such as, facilitate post-surgical tasks). Transmission of such audio and/or video feed can be initiated by the surgeon, for instance, via a user interface.

While certain steps of the process 1000 may be described as being manually performed by the RSC or another person, such steps can be performed automatically in some implementations. While certain steps of the process 1000 may be described as being performed by the orchestration application 432, such steps can be performed by other components of any of the remote surgery systems described herein, such as the system 400, 600, 625, or 675.

Outputting a Schedule

As described herein, a schedule can be output on the surgeon side, for instance, displayed on the monitor 414 connected to the surgeon PC 412. The schedule can be transmitted to the surgeon side by the orchestration application 432. Such schedule can pertain to the portion of the master schedule that includes only those scheduled surgical sessions that are scheduled to be performed by a surgeon. FIG. 9A illustrates an example schedule 1100 displayed on the surgeon side. The schedule 1100 can be displayed as a user interface on the monitor 414. The illustrated schedule 1100 can include scheduled surgical sessions for Dr. Robert Fisher. The schedule 1100 can include one or more lists or sets of scheduled surgical sessions 1102, 1104 grouped by operating rooms (such as, "BRMC Main OR 3" and "HVMC Main OR 15", which may be located in different physical locations (such as, in different hospitals "Frontline Health" and "Appalachia Healthcare"). Each of the operating rooms can include a patient-side surgical system can be remotely controlled by a surgeon. The schedule 1100 can list the scheduled surgical sessions in columns, in which the scheduled surgical sessions are ordered chronologically. Each session can be represented as an entry (such as, a cell) 1108 1110, 1112, 1114, and can correspond to a different patient and/or a different surgical procedure. Each cell can correspond to an allotted scheduled surgical session time slot for the surgical procedure.

Each scheduled surgical session can include the following: scheduled time for the surgical procedure (such as, "7:30a" in 1108), name of the one or more operating surgeons (such as, "Dr. Fisher/Dr. Fowler" in 1108), name of the patient (such as, "Chrysler, Bert" in 1108), type of surgical procedure (such as, "Gastric Bypass" in 1108), and patient and/or session status (such as, "Ready for Surgeon" in 1108, "In Pre-op" in 1110, "Scheduled" in 1112, "Closing," or "Canceled" in 1118).

The patient and/or session status can refer to a step in the process 1000. For example, "Scheduled" can indicate to a surgeon and the patient-side staff that the scheduled surgical session has been added to (or recorded in) the schedule, as described in connection with step 1008 of FIG. 8. As another example, "In Pre-op," can indicate that the patient has been moved to a pre-operating location, as described in connection with step 1016. As another example, "Ready for Surgeon" can indicate to the surgeon and patient-side staff that the patient is in the operating room and the remote surgery checklist should be reviewed by the surgeon and the patient-side staff, as described in connection with step 1022.

In some cases, a patient being scheduled for a surgical session ("Scheduled") indicates that a patient's scheduled surgical session has been added to the schedule, but the patient is not actively engaged in any pre-surgical, surgical or post-surgical activity. A patient in the pre-operation phase ("Pre-op") can indicate that the patient is at the patient-side location and is engaging with the patient-side medical staff to prepare for the surgical session. With reference to FIG. 9B, a patient who is in the operating room ("In Operating Room" as shown in the cell 1148) can mean that the patient has undergone pre-operation requirements and has been delivered to the operating room (for example, as described in step 1020 of FIG. 8). With reference to FIG. 9A, a patient who is ready for the surgery ("Ready for Surgeon") can mean that the patient has undergone pre-operation requirements, has been is physically placed in the operating room where the patient-side surgical system is located, and is in a position to be operated on once the surgeon completes the remote surgery checklist and takes control of the patient-side surgical system and performs remote surgery. When the surgical procedure has ended (or is about to end), the schedule 1100 can indicate that the patient is ready to be removed from the operating room ("Closing"). A scheduled surgical session being cancelled ("Canceled") indicates that the scheduled surgical session will no longer take place at the scheduled time.

In some cases, the schedule 1100 can include a session status (not shown) indicating initiation of a time window during which the surgeon is allowed to remotely control a patient-side robotic system to operate on a patient. For instance, such session status can be "Ready to Connect" or the like.

As is illustrated, scheduled surgical sessions being performed on different patients (and using different patient-side surgical systems) can overlap in time, such as 1108 and 1116 or 1117. That is, there can be different, overlapping time windows for operationally connecting surgical consoles to patient-side surgical systems. The sets of scheduled surgical sessions 1102, 1104 can be arranged in columns that overlap in time. For instance, time of the cell 1108 can overlap with time of the cell 1116 or 1117. Such overlap of the surgical sessions can allow the surgeon to enter a first scheduled surgical session immediately after completion of the pre-operation phase, complete the surgical procedure for such first session, then leave the first scheduled surgical session and enter a second scheduled surgical session while the first scheduled surgical session is in the closing phase. For example, Dr. Robert Fisher can complete a remote surgical operation on patient Aiden Howe (1116) and enter a surgical session for remotely operating on patient Bert Chrysler (1108) while patient Aiden Howe's surgery is being closed. In this configuration, the surgeon can optimize the surgeon's time by only entering scheduled surgical sessions when the surgeon is able to begin the surgical procedure and by promptly leaving surgical sessions when the surgeon's presence in no longer needed. Such optimization can minimize the surgeon's down time spent waiting for a patient to be ready for the procedure.

Overlapping time windows can optimize the surgeon's time as follows. For instance, overlapping first and second time windows can allow the same surgeon to perform a first surgical procedure on a first patient in the first time window and, after completing the first surgical procedure, quickly start performing a second surgical procedure on a second patient in the second time window. That is, a surgeon console collocated with and used by the surgeon can quickly switch between being operationally connected to allow the surgeon to remotely control a first patient-side surgical system when operating on the first patient to being operationally connected to allow the surgeon to remotely control a second patient-side surgical system for operating on the second patient. As another example, overlapping first and second time windows can allow a surgeon to remotely control the first patient-side surgical system to operate on the first patient and, following completion of the first surgical procedure by the first surgeon, facilitate a quick switch to allow another surgeon to remotely control the first patient-side surgical system to operate on the second patient.

Surgical sessions being performed on different patients may not overlap in time, such as 1110 and 1116. In such case, time windows associated with such non-overlapping surgical sessions would also be non-overlapping.

The schedule 1100 can include a summary 1101 that provides information for a patient that is ready to be operated on (such as, "Chrysler, Bert") and the next patient (such as, "Laflour, Maria"). The summary 1101 can provide a brief, easy-to-follow overview of surgical procedures ready to be performed at the present time as well as scheduled for the near future and can further optimize the surgeon's time.

One or more of sets of sessions, such as the set 1106, can be hidden (for instance, blurred or greyed out) so that confidential patient profile information cannot be viewed by unauthorized surgeons. The set of sessions 1106 can be scheduled for a different surgeon that the one associated with the schedule 1100.

FIG. 9B illustrates an example schedule 1130 displayed on the patient side. The schedule 1130 can be transmitted by the orchestration application 432 and displayed as a user interface on the nurse PC 420. Such schedule can pertain to the portion of the master schedule that includes only those scheduled surgical sessions that are scheduled to be performed at a particular surgeon side location. The schedule 1130 can include a list or set of surgical sessions 1144 scheduled at the particular patient-side location 1145 (such as, the operating room "BRMC Main OR 3, Frontline Health") associated with the schedule 1130. The set 1144 can correspond to the set 1102 illustrated in FIG. 9A. The set 1144 can be arranged as a column in which surgical sessions are ordered chronologically. Similarly to FIG. 9A, each entry of cell of the set 1144 can include one or more of the following: scheduled time for the surgical procedure (such as, "7:30a" in 1148), name of the one or more operating surgeons (such as, "Dr. Fisher/Dr. Fowler" in 1148), name of the patient (such as, "Chrysler, Bert" in 1148), type of surgical procedure (such as, "Gastric Bypass" in 1148), and patient and/or session status (such as, "Ready for Surgeon" in 1148).

The schedule 1130 can provide a list 1146 with information concerning one or more surgeons who will be performing the surgeries in the set 1144. Such information can include the name(s) 1149, 1158 of surgeon(s), the scheduled time(s) 1152, 1154, 1155 for surgical procedure(s), patient name(s) 1156, the location(s) 1160, 1172, 1174 of patient-side surgical system(s) controlled by the surgeon(s), the type(s) 1164 of surgical procedure(s), and the current status(es) 1166, 1168, 1170 of surgical procedure(s). Any of the locations 1160, 1172, 1174 can correspond to a location that may be different from the patient-side location 1145 associated with the schedule 1130. For instance, the location 1160 (such as, "HVC Main OR 15, Appalachia Healthcare") is different from the patient-side location 1145 (such as, "BRMC Main OR 3, Frontline Health"). This can indicate the surgeon is performing (or is scheduled to perform) a remote surgical procedure at a different patient-side location. This information can be provided to the operating room support staff at the patient-side location 1145 to assist with preparation of the patient for a surgical procedure that is scheduled to be performed at the patient-side location 1145.

The list 1146 can provide information for each of the surgeons who are scheduled to operate at the patient-side location 1145. For instance, the list provides information for the surgeons "Robert Fisher" and "Emmanuel Elliot." The provided information can include the current surgical procedure that a particular surgeon is performing and the next surgical procedure.

Certain information in the list 1146 can be hidden (for instance, blurred or greyed out) so that confidential patient information cannot be viewed by unauthorized operating room staff. As is illustrated by 1180, 1182, patient names and surgery types for patients not being operated on or scheduled to be operated on in the patient-side location 1145 can be hidden. Scheduled time(s) and current status(es) of the surgical procedure(s) for such patients can be exposed to assist with preparation of the patient for a surgical procedure that is scheduled to be performed at the patient-side location 1145.

The schedule 1130 can include a summary 1142 that provides information for the next patient (such as, "Obrien, Roman") scheduled to be operated on at the patient-side location 1145. The summary 1142 can also include information (not shown) for the current patient being operated on at the patient-side location 1145. The summary 1142 can provide a brief, easy-to-follow overview of the next scheduled surgical procedure (and, in some cases, for the current surgical procedure being performed) and can further optimize the surgeon's time by facilitating efficient preparation of the patient for the next scheduled surgical procedure.

Allowing Control of Robotic Surgery System

Granting control of a patient-side robotic surgery system to a surgeon operating a surgeon console directly implicates patient safety. When a surgeon is local to the patient-side robotic surgery system (such as, located in or near an operating room where the system and patient are placed), ensuring patient safety may be more straightforward than when the surgeon is located remotely. For example, in the local implementation, only one surgeon console would be connected to the patient-side robotic surgery system. In the remote example, in contrast, multiple surgeon consoles may be able to connect to the patient-side robotic surgery system, as described herein. Accordingly, the problem of ensuring patient safety prior to granting control is much more difficult to resolve in the remote surgery context. As described in this section, prior to granting control to the remote surgeon operating a remote surgeon console, various checks for controlling access to the patient-side robotic surgery system may need be performed to ensure that patient safety is not compromised.

Figure 10:
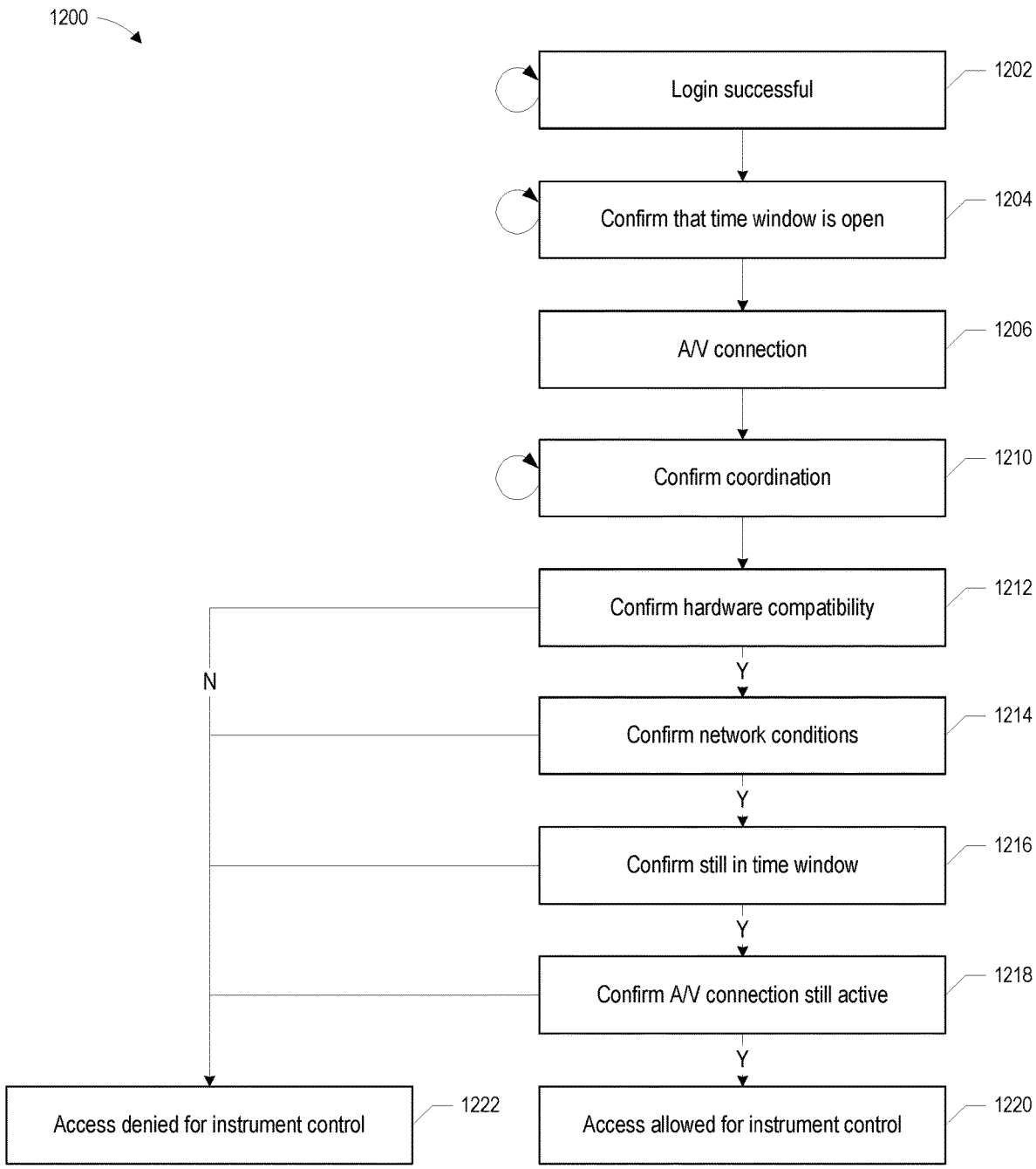
FIG. 10 is a block diagram of a process for allowing access for remotely controlling surgical procedures.

FIG. 10 illustrates a flow chart of a process 1200 for allowing remotely controlling a patient-side surgical system. The process 1200 can be implemented by any of the remote surgery systems described herein, such as the system 400, 600, 625, or 675. In some cases, the process 1200 can be implemented, at least in part, by the orchestration application 432. The process 1200 can be performed as part of processing a request to establish a session between a surgeon console collocated with a surgeon and a patient-side robotic surgery system collocated with a patient to allow the surgeon to remotely control movement and actuation of at least one surgical instrument (and/or at least one imaging system) of the patient-side robotic surgery system and operate on the patient.

The process 1200 can start at step 1202, where a surgeon can login to obtain access for remotely controlling at least one surgical instrument of a patient-side robotic surgery system. For example, the surgeon can enter the surgeon's login credentials (e.g., username and password) into a user interface of an application being executed on the surgeon PC 412. The surgeon PC 412 can communicate with the orchestration application 432, as described herein. In some examples, the orchestration application 432 can perform authentication of the login credentials. In some instances, when the surgeon inputs login credentials that fail the authentication service, the surgeon may not granted access to control the patient-side robotic surgery system. When the login is unsuccessful, step 1202 can be configured to loop and have the surgeon enter (or re-enter) login credentials to attempt to gain access. In some examples, the surgeon may not be able to remotely operate on the patient without verification of the surgeon's credentials.

At step 1204, once the surgeon has selected the desired surgery and patient (for instance, on the schedule 1100), the process 1200 can confirm that a time window for remotely operating on the patient is open, as described herein. In some instances, when the process 1200 determines that the time window is not open, step 1210 can be configured to loop and check again whether the time window is open. The surgeon may not be allowed to remotely operate on the patient outside the time window.

At step 1206, the process 1200 can wait for or establish an A/V connection between the surgeon side and the patient side. As described herein, the A/V connection can be established between the surgeon PC 412 and the telemedicine device 428 to facilitate provision of an audio and/or video feed from the patient site 404 to the surgeon site 402 (and vice versa) as well as facilitate a two-way audio and/or video communication between the patient site 404 and the surgeon site 402. The A/V connection can allow the surgeon and the operating room staff to communicate in real-time. In some examples, the surgeon may not be allowed to remotely operate on the patient without the A/V connection having been established.

At step 1210, the process 1200 can perform coordination between the patient side and the surgeon side. As described herein, coordination can generally refer to a handshake protocol being performed between the patient side and the surgeon side to ensure that both sides are ready for execution of a remotely controlled surgical procedure. As an example, coordination can involve completion of a checklist on the patient side and attestation of the checklist by the surgeon. The process 1200 can remain at step 1210 until coordination has been completed. In some examples, the surgeon may not be allowed to remotely to remotely operate on the patient until completion of coordination.

At step 1212, the process 1200 can verify compatibility between the patient-side surgical system and a surgeon console of the surgeon, as described herein. If compatibility is not verified, the process 1200 can transition to step 1222 where access to the patient-side robotic surgery system is denied.

If compatibility is verified, the process can transition to step 1214 where the process 1200 can confirm network conditions. As described herein, one or more networks connecting the surgeon console to the patient-side surgery system (such as, 208 or 430) can be selected and configured to reduce transmission delay and increase reliability and stability in order to remotely control the surgical procedure. Prior to allowing access to the patient-side robotic surgery system, the process 1200 (for instance, via the connectivity server 434) can verify that one or more networks connecting the surgeon console and the patient-side robotic surgery system meet network conditions (or network requirements) for remotely controlling the surgical procedure. In some examples, the process 1200 can perform one or more network tests to verify that the network conditions are satisfied. For instance, the connectivity server 434 may perform automated network tests on each endpoint on a cadence of, for example, every 30 minutes. The orchestration application 432 can query the connectivity server 434 to report the results of the most recent network test, or to initiate performance of a new network test. The connectivity server 434 can then analyze the one or more results of the network test to assess a quality of the connection. In some examples, the orchestration application 432 can perform the network test without involving the connectivity server 434.

In some examples, the network conditions can include one or more of network latency, network jitter, network packet loss, and network bandwidth. At step 1214, the process 1200 can assess whether the network conditions satisfy one or more threshold values. The process 1200 can verify that network latency satisfies a latency threshold, such as a value between about 1-2 ms and about 500 ms (such as, about 300 ms). Network latency verification can ensure that one or more networks are capable of reliably and quickly transferring image data of the surgical site (such as, video) from the patient side to the surgeon side, such that the surgeon can respond in a safe and timely manner to the image data. The process 1200 can assess whether network jitter satisfies a jitter threshold, such as below about 1 ms or below about 10 ms. Since network jitter causes variability in the latency of transmitted packets, it can affect the timing and order of control signals and image data. By verifying that network jitter does not exceed the jitter threshold, the process 1200 can ensure the reliable and prompt transfer of control signals and image data. The process 1200 can assess whether network packet loss satisfies a packet loss threshold, such as about 1% or about 5%. Packet loss verification can ensure that one or more networks are capable of reliably and quickly transferring control signals and image data. The process 1200 can assess whether network bandwidth satisfies a bandwidth threshold, such as at least about 1 Gigabit/second (Gb/s). Network bandwidth verification can ensure that one or more networks are capable of reliably and quickly transferring control signals and image data.

The one or more networks can include one or more primary and one or more secondary networks to provide for backup and/or redundant transmission of data between the surgeon side and the patient side. This can further facilitate robustness and reliability. In some examples, in step 1214, the process 1200 can confirm that a primary network connection satisfies the network conditions and that at least one secondary network connection is available. In some cases, the process 1200 can confirm in step 1214 that the at least one secondary network also satisfies at least some of the network conditions (or, in some cases, all of the network conditions).

Additional details of verifying network conditions are described in U.S. patent application Ser. No. 18/488,844, filed on Oct. 17, 2023, which is incorporated by reference in its entirety.

If the network conditions are not verified, the process 1200 can transition to step 1222 where access to the patient-side robotic surgery system is denied.

If the network conditions are verified, the process 1200 can transition to step 1216 where the process 1200 can confirm the time window remains open. If not, the process 1200 can transition to step 1222 where access to the patient-side robotic surgery system is denied.

If it is verified that the time window remains open, the process 1200 can transition to step 1218, where the process 1200 can confirm that the A/V connection remains active, to ensure the surgeon can maintain a dialog with the operating room staff during the surgical procedure. If not, the process 1200 can transition to step 1222 where access to the patient-side robotic surgery system is denied.

If it is verified that the A/V connection remains active, the process 1200 can transition to step 1220, where the process 1200 can grant access for remotely controlling at least one surgical instrument of the patient-side robotic surgery system. In some instances, the process 1200 can establish the session between the surgeon console and the patient-side robotic surgery system.

As described herein, at step 1222, the process 1200 can deny access for remotely controlling the patient-side robotic surgery system. For example, the process 1200 may block establishment of the session between the surgeon console and the patient-side robotic surgery system. The steps of the process 1200 can be executed in the illustrated order or in a different order. In some instances, one or more of the steps of the process 1200 can be optional and independent with respect to one another. In some instances, individual steps discussed above can be removed from the process 1200. In some instances, the process 1200 can include one or more additional or substitute verification tasks. For example, the process 1200 can perform one or more of: confirm surgical consent, confirm that a surgeon-side adapter (and/or the surgeon console) and a patient-side adapter (and/or the patient-side robotic surgery system) are in good health, verify a patient's identity, confirm a surgeon's licensing, provisioning, and certification, confirm the surgical procedure, confirm the surgeon completed a pre-operation visit, confirm the surgeon has a business relationship with patient-side site, or the like.

Surgical consent can be a form that the patient signed prior to the operation. For example, the patient can sign (for instance, physically or electronically) a consent form and the patient's consent can be recorded by the process 1200. In some cases, the process 1200 can present a user interface to provide the patient with an electronic surgical consent form and accept the patient's signature. In some instances, the process 1200 can verify surgical consent satisfied prior to granting access to remotely control the patient-side robotic surgery system.

Confirmation that the surgeon-side adapter (or, more generally, the surgeon console) and the patient-side adapter (or, more generally, the patient-side robotic surgery system) are in good health can include monitoring status information (such as, heartbeat signals or the like) transmitted by the respective adapters (or, more generally, by the surgeon console and the patient-side robotic surgery system). For example, status monitoring can be performed by the adapter management system 436. The adapter management system 436 can transmit status information to the orchestration application 432. In some examples, the orchestration application 432 can query the adapter management system 436 to for status information. In response, the adapter management system 436 can provide received status information or ping the respective adapters (or, more generally, the surgeon console and the patient-side robotic surgery system) for status information. Based on the status information, the orchestration application 432 can assess whether the health of the respective adapters (or, more generally, the surgeon console and the patient-side robotic surgery system) is satisfactory for remote surgery. In some examples, access to the patient-side robotic surgery system can be restricted if the status of any of the adapters (or, more generally, of the surgeon console or the patient-side robotic surgery system) indicates bad health (for instance, the reported status indicates an error or no status has been reported).

Verification of the patient identity can include comparing the patient in the operating room to the patient listed in the schedule. Such verification can be part of the coordination in step 1210. In some examples, the orchestration application 432 can prompt medical personnel in the operating room to confirm the identity of the patient prior to the surgeon gaining access to the patient-side robotic surgery system. Medical personnel can provide confirmation of the patient with the orchestration application 432, such as via a user interface (for instance, a checkbox), verbally (for instance, via the A/V connection or using a telephone), or the like. In some examples, verification of the patient identity can include verifying the patient's biometric information. For example, the verification can include a comparison of a fingerprint scan of the patient at the time of operation with a recorded fingerprint of the patient prior to the time of operation. The orchestration application 432 can be configured to receive the fingerprint scan and compare the scan with the recorded fingerprint of the patient. Access may be granted to the surgeon only in response to the comparison resulting in a positive match between the fingerprints. Other biometric information can be used in a similar manner to verify the identity of the patient.

Verification procedure for granting access to control the patient-side robotic surgery system can include checking that the surgery being performed is the surgery scheduled for the patient. For example, the orchestration application 432 can prompt medical personnel in the operating room to confirm the surgical procedure is the scheduled surgical procedure. This can be performed using any of the approaches described herein, such as, via a user interface, vocally, or the like. Access may be granted only in response to a match between the surgical procedures.

Verification procedure for granting access can include confirming the surgeon's professional credentials, such as one or more of licensing, provisioning, and certification. The professional credentials can indicate permission to perform particular type of surgery, right to perform surgery at a particular hospital or medical center, or the like. Verification procedure for granting access can include confirmation that the surgeon completed a pre-operation visit and confirmation that the surgeon has a business relationship with the particular hospital or medical center. These verifications can be performed using any of the approaches described herein, such as, via a user interface, vocally, or the like.

Providing access for controlling the patient-side robotic surgery system can involve transmission of control signals for moving and actuating at least one instrument of the patient-side robotic surgery system. Prior to transmission of such control signals, it may be necessary to establish the A/V connection that provides a two-way audio and/or video communication between the patient side and the surgeon side as well as well as arrange for transmission of image data of the surgical site to the surgeon side. It may be unsafe to allow the surgeon to operate on the patient if the surgeon were not able to have a dialog with the patient-side surgical staff via the A/V connection. For example, the surgical staff may verbally communicate a patient-side issue that would require the remote surgeon to discontinue or alter the operation of one or more instruments. Additionally, it can be advantageous for the surgeon to communicate with the surgical staff prior to initiating the surgical procedure in order to talk through coordination or the like. Further, it may be unsafe to allow the surgeon to operate one or more instruments if the surgeon were not seeing the live results of that operation via the transmitted image data of the surgical site.

The process 1200 may grant access for remotely controlling at least one surgical instrument of the patient-side robotic surgery system after it has verified that 1) the A/V connection has been established and 2) the image data is ready to be transmitted or is being transmitted. In some implementations, the A/V connection can be established prior to commencement of transmission of the image data or substantially simultaneously with commencement of transmission of the image data (which can encompass a time period after commencement of transmission of the image data). For example, the A/V connection can be established within 2 seconds of commencement of transmission of the image data (such as, up to 2 seconds after commencement of transmission of the image data). In certain cases, control signals may be transmitted after transmission of the image data has commenced or substantially simultaneously with transmission of the image data (which can encompass a time period prior to commencement of transmission of the image data). For example, commencement of transmission of the control data can be within 500 ms of commencement of transmission of the image data (such as, up to 500 ms before commencement of transmission of the image data).

Example Implementations

Example Implementation 1: A system for remotely controlling robotic surgery, the system comprising:
- a plurality of surgeon-side adapters each configured to be integrated with a corresponding surgeon console of a plurality of surgeon consoles, the plurality of surgeon consoles being configured to control surgical instruments and imaging systems of a plurality of patient-side robotic surgery systems of different types, the plurality of surgeon-side adapters and the plurality of surgeon consoles being configured to be located remotely from the plurality of patient-side robotic surgery systems;
- a plurality of patient-side adapters each configured to be integrated with a patient-side robotic surgery system of the plurality of patient-side robotic surgery systems each including at least one surgical instrument and at least one imaging system, the plurality of patient-side robotic surgery systems including a first plurality of patient-side robotic surgery systems of a first type and a second plurality of patient-side robotic surgery systems of a second type different from the first type; and a non-transitory computer readable medium storing instructions that, when executed by one or more processors, cause the one or more processors to:

verify that a first surgeon console and a first patient-side robotic surgery system are both of the first type;

subsequent to verifying that the first surgeon console and the first patient-side robotic surgery system are both of the first type, establish a first session between a first surgeon-side adapter integrated with the first surgeon console and a first patient-side adapter integrated with the first patient-side robotic surgery system to allow the first surgeon console to remotely control movement and actuation of the at least one surgical instrument and the at least one imaging system of the first patient-side robotic surgery system;

verify that a second surgeon console and a second patient-side robotic surgery system are both of the second type; and subsequent to verifying that the second surgeon console and the second patient-side robotic surgery system are both of the second type, establish a second session to allow the second surgeon console with which a second surgeon-side adapter is integrated to remotely control movement and actuation of the at least one surgical instrument and the at least one imaging system of the second patient-side robotic surgery system.

Example Implementation 2: The system of example implementation 1, wherein the instructions further cause the one or more processors to:

in response to not verifying that the second surgeon console and the second patient-side robotic surgery system are both of the second type, block establishment of the second session to prevent the second surgeon console from remotely controlling movement and actuation of the at least one surgical instrument and the at least one imaging system of the second patient-side robotic surgery system.

Example Implementation 3: The system of any of example implementations 1 to 2, wherein the instructions further cause the one or more processors to:

in response to not verifying that the first surgeon console and the first patient-side robotic surgery system are both of the first type, block establishment of the first session to prevent the first surgeon console from remotely controlling movement and actuation of the at least one surgical instrument and the at least one imaging system of the first patient-side robotic surgery system.

Example Implementation 4: The system of any of example implementations 1 to 3, wherein the first type is indicative of at least one of a first manufacturer, first model, or first program instructions of the first plurality of patient-side robotic surgery systems and the second type is indicative of at least one of a second manufacturer, second model, or second program instructions of the second plurality of patient-side robotic surgery systems.

Example Implementation 5: The system of any of example implementations 1 to 4, wherein the first session comprises transmission of:

one or more control commands for movement and actuation of the at least one surgical instrument and the at least one imaging system of the first patient-side robotic surgery system;

status information of the first patient-side robotic surgery system; and image data obtained by the at least one imaging system of the first patient-side robotic surgery system.

Example Implementation 6: The system of example implementation 5, wherein the instructions further cause the one or more processors to transmit from the first patient-side adapter to the first surgeon-side adapter image data obtained by the at least one imaging system prior to establishment of the first session.

Example Implementation 7: The system of any of example implementations 1 to 6, wherein the instructions further cause the one or more processors to transmit an internet protocol (IP) address of the first patient-side adapter to the first surgeon-side adapter to cause the first patient-side adapter and the first surgeon-side adapter to establish a peer-to-peer connection using the IP address.

Example Implementation 8: The system of any of example implementations 1 to 7, wherein the instructions cause the one or more processors to verify that that the second surgeon console and the second patient-side robotic surgery system are both of the second type prior to establishing the first session.

Example Implementation 9: The system of any of example implementations 1 to 8, wherein instructions cause the one or more processors to:

establish the first session subsequent to 1) verifying that the first surgeon console and the first patient-side robotic surgery system are both of the first type and 2) verifying that coordination between a first surgeon collocated with the first surgeon console and first patient staff collocated with the first patient-side robotic surgery system has been completed; and establish the second session subsequent to 1) verifying that the second surgeon console and the second patient-side robotic surgery system are both of the second type and 2) verifying that coordination between a second surgeon collocated with the second surgeon console and second patient staff collocated with the second patient-side robotic surgery system has been completed.

Example Implementation 10: A system for remotely controlling robotic surgery, the system comprising:

a surgeon-side adapter configured to be integrated with a surgeon console, the surgeon console configured to control surgical instruments and imaging systems of a first plurality of patient-side robotic surgery systems of a first type, the surgeon-side adapter and the surgeon console being configured to be located remotely from the first plurality of patient-side robotic surgery systems of the first type;

a plurality of patient-side adapters each configured to be integrated with a patient-side robotic surgery system of a second plurality of patient-side robotic surgery systems each including at least one surgical instrument and at least one imaging system, the second plurality of patient-side robotic surgery systems including the first plurality of patient-side robotic surgery systems of the first type and at least one patient-side robotic surgery system of a second type different from the first type; and a non-transitory computer readable medium storing instructions that, when executed by one or more processors, cause the one or more processors to:
  verify that the surgeon console and a first patient-side robotic surgery system are both of the first type;
  subsequent to verifying that the surgeon console and the first patient-side robotic surgery system are both of the first type, establish a first session between a surgeon-side adapter integrated with the surgeon console and a first patient-side adapter integrated with the first patient-side robotic surgery system to allow the surgeon console to remotely control movement and actuation of the at least one surgical instrument and the at least one imaging system of the first patient-side robotic surgery system;
  verify that a second patient-side robotic surgery system is of the second type; and
  subsequent to verifying that the second patient-side robotic surgery system is of the second type, block establishment of a second session between the surgeon-side adapter and a second patient-side adapter integrated with the second patient-side robotic surgery system to prevent the surgeon console from remotely controlling movement and actuation of the at least one surgical instrument and the at least one imaging system of the second patient-side robotic surgery system.

Example Implementation 11: The system of example implementation 10, wherein the instructions further cause the one or more processors to:
  verify that the second patient-side robotic surgery system is of the first type; and
  subsequent to verifying that the second patient-side robotic surgery system is of the first type, establish the second session to allow the surgeon console to remotely control movement and actuation of the at least one surgical instrument and the at least one imaging system of the second patient-side robotic surgery system.

Example Implementation 12: The system of any of example implementations 10 to 11, wherein the first type is indicative of at least one of a first manufacturer, first model, or first program instructions of the first plurality of patient-side robotic surgery systems and the second type is indicative of at least one of a second manufacturer, second model, or second program instructions of the at least one patient-side robotic surgery system of the second type.

Example Implementation 13: The system of any of example implementations 10 to 12, wherein the first session comprises transmission of:
  one or more control commands for movement and actuation of the at least one surgical instrument and the at least one imaging system of the first patient-side robotic surgery system;
  status information of the first patient-side robotic surgery system; and
  image data obtained by the at least one imaging system of the first patient-side robotic surgery system.

Example Implementation 14: The system of example implementation 13, wherein the instructions further cause the one or more processors to transmit from the first patient-side adapter to the surgeon-side adapter image data obtained by the at least one imaging system prior to establishment of the first session.

Example Implementation 15: The system of any of example implementations 10 to 14, wherein the instructions further cause the one or more processors to transmit an internet protocol (IP) address of the first patient-side adapter to the surgeon-side adapter to cause the first patient-side adapter and the surgeon-side adapter establish a peer-to-peer connection using the IP address.

Example Implementation 16: A system for remotely controlling robotic surgery, the system comprising:
  a plurality of surgeon-side adapters each configured to be integrated with a corresponding surgeon console of a plurality of surgeon consoles, the plurality of surgeon consoles configured to control surgical instruments and imaging systems of a patient-side robotic surgery system of a first type and at least one other patient-side robotic surgery system of a second type different from the first type, the plurality of surgeon-side adapters and the plurality of surgeon consoles being configured to be located remotely from the patient-side robotic surgery system and the at least one other patient-side robotic surgery system;
  a patient-side adapter configured to be integrated with the patient-side robotic surgery system including at least one surgical instrument and at least one imaging system; and
  a non-transitory computer readable medium storing instructions that, when executed by one or more processors, cause the one or more processors to:
    verify that a first surgeon console and the patient-side robotic surgery system are both of the first type;
    subsequent to verifying that the first surgeon console and the patient-side robotic surgery system are both of the first type, establish a first session between a first surgeon-side adapter integrated with the first surgeon console and a patient-side adapter integrated with the patient-side robotic surgery system to allow the first surgeon console to remotely control movement and actuation of the at least one surgical instrument and the at least one imaging system of the patient-side robotic surgery system;
    verify that a second surgeon console is of the second type; and
    subsequent to verifying that the second surgeon console is of the second type, block establishment of a second session between a second surgeon-side adapter integrated with the second surgeon console and the patient-side adapter to prevent the second surgeon console from remotely controlling movement and actuation of the at least one surgical instrument and the at least one imaging system of the patient-side robotic surgery system.

Example Implementation 17: The system of example implementation 16, wherein the instructions further cause the one or more processors to:
  verify that the second surgeon console is of the first type; and
  subsequent to verifying that the second surgeon console is of the first type, establish the second session to allow the second surgeon console to remotely control movement and actuation of the at least one surgical instrument and the at least one imaging system of the patient-side robotic surgery system.

Example Implementation 18: The system of any of example implementations 16 to 17, wherein the first type is indicative of at least one of a first manufacturer, first model, or first program instructions of the patient-side robotic surgery system and the second type is indicative of at least one of a second manufacturer, second model, or second program instructions of the at least one other patient-side robotic surgery system of the second type.

Example Implementation 19: The system of any of example implementations 16 to 18, wherein the first session comprises transmission of:
- one or more control commands for movement and actuation of the at least one surgical instrument and the at least one imaging system of the patient-side robotic surgery system;
- status information of the patient-side robotic surgery system; and
- image data obtained by the at least one imaging system of the patient-side robotic surgery system.

Example Implementation 20: The system of example implementation 19, wherein the instructions further cause the one or more processors to transmit from the patient-side adapter to the first surgeon-side adapter image data obtained by the at least one imaging system prior to establishment of the first session.

Example Implementation 21: The system of any of example implementations 16 to 20, wherein the instructions further cause the one or more processors to transmit an internet protocol (IP) address of the patient-side adapter to the first surgeon-side adapter to cause the patient-side adapter and the first surgeon-side adapter to establish a peer-to-peer connection using the IP address.

Example Implementation 22: A system for remotely controlling robotic surgery, the system comprising:
- a plurality of surgeon-side adapters configured to be integrated with a plurality of surgeon consoles, each surgeon console being configured to control at least one surgical instrument and at least one imaging system of a patient-side robotic surgery system located remotely from the surgeon console and a surgeon-side adapter integrated with the surgeon console;
- a plurality of patient-side adapters each configured to be integrated with a respective patient-side robotic surgery system; and
- a non-transitory computer readable medium storing instructions that, when executed by one or more processors, cause the one or more processors to:
  - create a first schedule of remote surgeries for a first surgeon, the first schedule including a first plurality of patients and a first plurality of patient-side robotic surgery systems configured to be controlled by the first surgeon to operate on the first plurality of patients;
  - transmit the first schedule to a first surgeon-side computing device and cause the first schedule to be displayed by the first surgeon-side computing device;
  - create a second schedule of remote surgeries for a second surgeon different than the first surgeon, the second schedule including a second plurality of patients and a second plurality of patient-side robotic surgery systems configured to be controlled by the second surgeon to operate on the second plurality of patients;
  - transmit the second schedule to a second surgeon-side computing device and cause the second schedule to be displayed by the second surgeon-side computing device;
  - subsequent to transmission of the first schedule, receive a first request to establish a first session between a first surgeon console collocated with the first surgeon and a first patient-side robotic surgery system of the first plurality of patient-side robotic surgery systems to allow the first surgeon to remotely control movement and actuation of at least one surgical instrument and at least one imaging system of the first patient-side robotic surgery system and operate on a first patient of the first plurality of patients;
  - verify that the first request is received within a first time window for operating on the first patient; and
  - in response to verifying that the first request has been received within the first time window, establish the first session between a first surgeon-side adapter integrated with the first surgeon console and a first patient-side adapter integrated with the first patient-side robotic surgery system to allow the first surgeon to remotely control movement and actuation of at least one surgical instrument and at least one imaging system of the first patient-side robotic surgery system and operate on the first patient.

Example Implementation 23: The system of example implementation 22, wherein the instructions further cause the one or more processors to:
- in response to determining that the first time window has been opened, transmit to the first surgeon-side computing device an indication that the first request can be initiated and cause display, by the first surgeon-side computing device, of the indication on the first schedule.

Example Implementation 24: The system of any of example implementations 22 to 23, wherein the instructions further cause the one or more processors to:
- receive a second request to establish a second session between the first surgeon console and a second patient-side robotic surgery system of the first plurality of patient-side robotic surgery systems to allow the first surgeon to remotely control movement and actuation of at least one surgical instrument and at least one imaging system of the second patient-side robotic surgery system and operate on a second patient of the first plurality of patients;
- verify that the second request is received within a second time window for operating on the second patient, the second time window overlapping the first time window; and
- in response to verifying that the second request has been received within the second time window, establish the second session between the first surgeon-side adapter and a second patient-side adapter integrated with the second patient-side robotic surgery system to allow the first surgeon to remotely control movement and actuation of at least one surgical instrument and at least one imaging system of the second patient-side robotic surgery system and operate on the second patient.

Example Implementation 25: The system of any of example implementations 22 to 24, wherein the second schedule further includes at least one patient from the first plurality of patients and at least one patient-side robotic surgery system of the first plurality of patient-side robotic surgery systems, and wherein the instructions further cause the one or more processors to:
- subsequent to transmission of the second schedule, receive a second request to establish a second session between a second surgeon console collocated with the second surgeon and the first patient-side robotic surgery system to allow the second surgeon to remotely control movement and actuation of at least one surgical instrument and at least one imaging system of the first patient-side robotic surgery system and operate on a second patient of the first plurality of patients;

verify that the second request is received within a second time window for operating on the second patient, the second time window not overlapping the first time window; and in response to verifying that the second request has been received within the second time window, establish the second session between a second surgeon-side adapter integrated with the second surgeon console and the first patient-side adapter to allow the second surgeon to remotely control movement and actuation of at least one surgical instrument and at least one imaging system of the first patient-side robotic surgery system and operate on the second patient.

Example Implementation 26: The system of any of example implementations 22 to 25, wherein the instructions further cause the one or more processors to, in response to verifying that the first request has been received within the first time window:

prior to establishing the first session, establish a connection between the first surgeon-side computing device and an audio-visual system located in an operating room where the first patient-side robotic surgery system and the first patient are located, the audio-visual system being configured to facilitate a two-way audio and video communication between a surgeon collocated with the first surgeon console and one or more medical personnel in the operating room.

Example Implementation 27: The system of any of example implementations 22 to 26, wherein the first session comprises transmission of:

one or more control commands for movement and actuation of the at least one surgical instrument and the at least one imaging system of the first patient-side robotic surgery system;

status information of the first patient-side robotic surgery system; and image data obtained by the at least one imaging system of the first patient-side robotic surgery system.

Example Implementation 28: The system example implementation 27, wherein the instructions further cause the one or more processors to transmit from the first patient-side adapter to the first surgeon-side adapter image data obtained by the at least one imaging system prior to establishment of the first session.

Example Implementation 29: A system for remotely controlling robotic surgery, the system comprising:

a plurality of surgeon-side adapters configured to be integrated with a plurality of surgeon consoles, each surgeon console being configured to control at least one surgical instrument and at least one imaging system of a patient-side robotic surgery system located remotely from the surgeon console and a surgeon-side adapter integrated with the surgeon console;

a plurality of patient-side adapters each configured to be integrated with a respective patient-side robotic surgery system; and a non-transitory computer readable medium storing instructions that, when executed by one or more processors, cause the one or more processors to:

create a first schedule of remote surgeries for a first surgeon, the first schedule including a first plurality of patients and a first plurality of patient-side robotic surgery systems configured to be controlled by the first surgeon to operate on the first plurality of patients;

transmit the first schedule to a first surgeon-side computing device and cause the first schedule to be displayed by the first surgeon-side computing device;

determine that a first time window for operating on a first patient of the first plurality of patients has been opened;

in response to determining that the first time window has been opened, transmit to the first surgeon-side computing device a first indication that a first request can be initiated to establish a first session between a first surgeon console collocated with the first surgeon and a first patient-side robotic surgery system of the first plurality of patient-side robotic surgery systems to allow the first surgeon to remotely control movement and actuation of at least one surgical instrument and at least one imaging system of the first patient-side robotic surgery system and operate on the first patient;

subsequent to transmission of the first indication, receive the first request;

verify that the first request is received within the first time window for operating on the first patient; and in response to verifying that the first request has been received within the first time window, establish the first session between a first surgeon-side adapter integrated with the first surgeon console and a first patient-side adapter integrated with the first patient-side robotic surgery system to allow the first surgeon to remotely control movement and actuation of at least one surgical instrument and at least one imaging system of the first patient-side robotic surgery system and operate on the first patient.

Example Implementation 30: The system of example implementation 29, wherein the instructions further cause the one or more processors to cause display, by the first surgeon-side computing device, of the first indication on the first schedule.

Example Implementation 31: The system of any of example implementations 29 to 30, wherein the instructions further cause the one or more processors to:

determine that a second time window for operating on a second patient of the first plurality of patients has been opened;

in response to determining that the second time window has been opened, transmit to the first surgeon-side computing device a second indication that a second request can be initiated to establish a second session between the first surgeon console and a second patient-side robotic surgery system of the first plurality of patient-side robotic surgery systems to allow the first surgeon to remotely control movement and actuation of at least one surgical instrument and at least one imaging system of the second patient-side robotic surgery system and operate on the second patient;

subsequent to transmission of the second indication, receive the second request;

verify that the second request is received within the second time window for operating on the second patient; and in response to verifying that the second request has been received within the second time window, establish the second session between the first surgeon-side adapter and a second patient-side adapter integrated with the second patient-side robotic surgery system to allow the first surgeon to remotely control movement and actuation of at least one surgical instrument and at least one imaging system of the second patient-side robotic surgery system and operate on the second patient.

Example Implementation 32: The system of example implementation 31, wherein the first time window overlaps with the second time window.

Example Implementation 33: The system of example implementation 31, wherein the first time window does not overlap with the second time window.

Example Implementation 34: The system of any of example implementations 29 to 33, wherein the instructions further cause the one or more processors to:
  create a second schedule of remote surgeries for a second surgeon different than the first surgeon, the second schedule including 1) a second plurality of patients and a second plurality of patient-side robotic surgery systems configured to be controlled by the second surgeon to operate on the second plurality of patients and 2) at least one patient from the first plurality of patients and at least one patient-side robotic surgery system of the first plurality of patient-side robotic surgery systems;
  transmit the second schedule to a second surgeon-side computing device and cause the second schedule to be displayed by the second surgeon-side computing device;
  determine that a second time window for operating on a second patient of the first plurality of patients has been opened, the second time window not overlapping with the first time window;
  in response to determining that the second time window has been opened, transmit to the second surgeon-side computing device a second indication that a second request can be initiated to establish a second session between a second surgeon console collocated with the second surgeon and the first patient-side robotic surgery system to allow the second surgeon to remotely control movement and actuation of at least one surgical instrument and at least one imaging system of the first patient-side robotic surgery system and operate on the second patient;
  subsequent to transmission of the second indication, receive the second request;
  verify that the second request is received within the second time window for operating on the second patient; and
  in response to verifying that the second request has been received within the second time window, establish the second session between a second surgeon-side adapter integrated with the second surgeon console and the first patient-side adapter to allow the second surgeon to remotely control movement and actuation of at least one surgical instrument and at least one imaging system of the first patient-side robotic surgery system and operate on the second patient.

Example Implementation 35: The system of any of example implementations 29 to 34, wherein the instructions further cause the one or more processors to:
  create a second schedule of remote surgeries for a second surgeon different than the first surgeon, the second schedule including a second plurality of patients and a second plurality of patient-side robotic surgery systems configured to be controlled by the second surgeon to operate on the second plurality of patients;
  transmit the second schedule to a second surgeon-side computing device and cause the second schedule to be displayed by the second surgeon-side computing device;
  determine that a second time window for operating on a second patient of the second plurality of patients has been opened, the second time window overlapping with the first time window;
  in response to determining that the second time window has been opened, transmit to the second surgeon-side computing device a second indication that a second request can be initiated to establish a second session between a second surgeon console collocated with the second surgeon and a second patient-side robotic surgery system of the second plurality of patient-side robotic surgery systems to allow the second surgeon to remotely control movement and actuation of at least one surgical instrument and at least one imaging system of the second patient-side robotic surgery system and operate on the second patient;
  subsequent to transmission of the second indication, receive the second request;
  verify that the second request is received within the second time window for operating on the second patient; and
  in response to verifying that the second request has been received within the second time window, establish the second session between a second surgeon-side adapter integrated with the second surgeon console and a second patient-side adapter integrated with the second patient-side robotic surgery system to allow the second surgeon to remotely control movement and actuation of at least one surgical instrument and at least one imaging system of the second patient-side robotic surgery system and operate on the second patient.

Example Implementation 36: The system of any of example implementations 29 to 35, wherein the instructions further cause the one or more processors to, in response to verifying that the first request has been received within the first time window:
  prior to establishing the first session, establish a connection between the first surgeon-side computing device and an audio-visual system located in an operating room where the first patient-side robotic surgery system and the first patient are located, the audio-visual system being configured to facilitate a two-way audio and video communication between a surgeon collocated with the first surgeon console and one or more medical personnel in the operating room.

Example Implementation 37: The system of any of example implementations 29 to 36, wherein the first session comprises transmission of:
  one or more control commands for movement and actuation of the at least one surgical instrument and the at least one imaging system of the first patient-side robotic surgery system;
  status information of the first patient-side robotic surgery system; and
  image data obtained by the at least one imaging system of the first patient-side robotic surgery system.

Example Implementation 38: The system of example implementation 37, wherein the instructions further cause the one or more processors to transmit from the first patient-side adapter to the first surgeon-side adapter image data obtained by the at least one imaging system prior to establishment of the first session.

Example Implementation 39: At least one non-transitory computer readable medium storing instructions that, when executed by one or more processors, cause the one or more processors to:

create a first schedule of remote surgeries for a first surgeon, the first schedule including temporally ordered pairs of a first plurality of patients and a first plurality of patient-side robotic surgery systems configured to be controlled by the first surgeon to operate on the first plurality of patients, at least some patient-side robotic surgery systems of the first plurality of patient-side robotic surgery systems being located in different physical locations, and a first pair including a first patient and a first patient-side robotic surgery system overlapping in time with a second pair including a second patient and a second patient-side robotic surgery system located in a different physical location than the first patient-side robotic surgery system;

transmit the first schedule to a first surgeon-side computing device and cause the first schedule to be displayed by the first surgeon-side computing device;

subsequent to transmission of the first schedule, transmit to the first surgeon-side computing device a first indication that a first request can be initiated to establish a first session between a first surgeon console collocated with the first surgeon and the first patient-side robotic surgery system to allow the first surgeon to remotely control movement and actuation of at least one surgical instrument and at least one imaging system of the first patient-side robotic surgery system and operate on the first patient;

subsequent to transmission of the first indication, receive the first request; and subsequent to receipt of the first request, establish the first session between the first surgeon console and the first patient-side robotic surgery system to allow the first surgeon to remotely control movement and actuation of at least one surgical instrument and at least one imaging system of the first patient-side robotic surgery system and operate on the first patient.

Example Implementation 40: The at least one non-transitory computer readable medium of example implementation 39, wherein the instructions further cause the one or more processors to:

subsequent to establishment of the first session, transmit to the first surgeon-side computing device a second indication that a second request can be initiated to establish a second session between the first surgeon console collocated with the first surgeon and the second patient-side robotic surgery system to allow the first surgeon to remotely control movement and actuation of at least one surgical instrument and at least one imaging system of the second patient-side robotic surgery system and operate on a second patient;

subsequent to transmission of the second indication, receive the second request; and subsequent to receipt of the second request, establish the second session between the first surgeon console and second patient-side robotic surgery system to allow the first surgeon to remotely control movement and actuation of at least one surgical instrument and at least one imaging system of the second patient-side robotic surgery system and operate on the second patient.

Example Implementation 41: The at least one non-transitory computer readable medium of example implementation 40, wherein the instructions further cause the one or more processors to:

transmit the first indication in response to determining that a first time window for operating on the first patient has been opened;

establish the first session in response to verifying that the first request has been received within the first time window;

transmit the second indication in response to determining that a second time window for operating on the second patient has been opened, the second time window overlapping with the first time window; and establish the second session in response to verifying that the second request has been received within the second time window.

Example Implementation 42: The at least one non-transitory computer readable medium of any of example implementations 40 to 41, wherein the instructions further cause the one or more processors to:

transmit the first indication in response to determining that a first time window for operating on the first patient has been opened; and establish the first session in response to verifying that the first request has been received within the first time window.

Example Implementation 43: A system for remotely controlling robotic surgery, the system comprising:

a plurality of surgeon-side adapters configured to be integrated with a plurality of surgeon consoles, each surgeon console being configured to control at least one surgical instrument and at least one imaging system of a patient-side robotic surgery system of a plurality of patient-side robotic surgery systems, the patient-side robotic surgery system being located remotely from the surgeon console and a surgeon-side adapter integrated with the surgeon console;

a plurality of patient-side adapters each configured to be integrated with a respective patient-side robotic surgery system; and at least one non-transitory computer readable medium storing instructions that, when executed by one or more processors, cause the one or more processors to:

receive a request to establish a session between a surgeon console of the plurality of surgeon consoles and a patient-side robotic surgery system of the plurality of patient-side robotic surgery systems to allow a surgeon with whom the surgeon console is collocated to remotely control movement and actuation of at least one surgical instrument and at least one imaging system of the patient-side robotic surgery system and operate on a patient collocated with the patient-side robotic surgery system; and establish the session between a surgeon-side adapter of the plurality of surgeon-side adapters, the surgeon-side adapter being integrated with the surgeon console, and a patient-side adapter of the plurality of patient-side adapters, the patient-side adapter being integrated with the patient-side robotic surgery system, in response to:

verifying that a connection has been established between a surgeon-side computing device and an audio-visual system located in an operating room where the patient-side robotic surgery system and the patient are located, the audio-visual system being configured to facilitate a two-way communication between the surgeon and one or more medical personnel in the operating room;

verifying that the surgeon console is compatible with the patient-side robotic surgery system; and verifying that at least one network connection between the surgeon-side adapter and the patient-side adapter satisfies at least one network condition criterion.

Example Implementation 44: The system of example implementation 43, wherein the instructions cause the one or more processors to:
establish the session between the surgeon console and the patient-side robotic surgery system further in response to verifying that coordination has been completed between the surgeon and the one or more medical personnel in the operating room.

Example Implementation 45: The system of example implementation 44, wherein coordination comprises confirming that: the surgeon is ready to operate on the patient, the patient has been prepared for being operated on, and the patient-side robotic surgery system has been prepared for operating on the patient.

Example Implementation 46: The system of any of example implementations 43 to 45, wherein the instructions cause the one or more processors to:
establish the session between the surgeon console and the patient-side robotic surgery system further in response to verifying that the request has been received within a time window for operating on the patient.

Example Implementation 47: The system of example implementation 46, wherein the time window corresponds to a scheduled time for operating on the patient.

Example Implementation 48: The system of any of example implementations 43 to 47, wherein the instructions cause the one or more processors to:
establish the session between the surgeon console and the patient-side robotic surgery system further in response to verifying login credentials of the surgeon.

Example Implementation 49: The system of any of example implementations 43 to 48, wherein verifying that the at least one network connection between the surgeon-side adapter and the patient-side adapter satisfies the at least one network condition criterion comprises:
verifying that latency of the at least one network connection satisfies a latency threshold;
verifying that jitter over the at least one network connection satisfies a jitter threshold;
verifying that packet loss of the at least one network connection satisfies a packet loss threshold; and
verifying that bandwidth of the at least one network connection satisfies a bandwidth threshold.

Example Implementation 50: The system of any of example implementations 43 to 49, wherein verifying that the at least one network connection between the surgeon-side adapter and the patient-side adapter satisfies at least one network condition criterion comprises:
verifying that the at least one network connection comprises at least two network connections between the surgeon-side adapter and the patient-side adapter.

Example Implementation 51: At least one non-transitory computer readable medium storing instructions that, when executed by one or more processors, cause the one or more processors to:
receive a request to establish a session between a surgeon console collocated with a surgeon and a patient-side robotic surgery system collocated with a patient to allow the surgeon to remotely control movement and actuation of at least one surgical instrument and at least one imaging system of the patient-side robotic surgery system and operate on the patient collocated; and
establish the session between the surgeon console and the patient-side robotic surgery system in response to:
verifying that a connection has been established between a surgeon-side computing device and an audio-visual system located in an operating room where the patient-side robotic surgery system and the patient are located, the audio-visual system being configured to facilitate a two-way video communication between the surgeon and one or more medical personnel in the operating room;
verifying that the surgeon console is compatible with the patient-side robotic surgery system; and
verifying that at least one network connection between the surgeon console and the patient-side robotic surgery system satisfies at least one network condition criterion.

Example Implementation 52: The at least one non-transitory computer readable medium of example implementation 51, wherein the instructions cause the one or more processors to:
establish the session between the surgeon console and the patient-side robotic surgery system further in response to verifying that coordination has been completed between the surgeon and the one or more medical personnel in the operating room.

Example Implementation 53: The at least one non-transitory computer readable medium of example implementation 52, wherein coordination comprises confirming that: the surgeon is ready to operate on the patient, the patient has been prepared for being operated on, and the patient-side robotic surgery system has been prepared for operating on the patient.

Example Implementation 54: The at least one non-transitory computer readable medium of any of example implementations 51 to 53, wherein the instructions cause the one or more processors to:
establish the session between the surgeon console and the patient-side robotic surgery system further in response to verifying that the request has been received within a time window for operating on the patient.

Example Implementation 55: The at least one non-transitory computer readable medium of example implementation 54, wherein the time window corresponds to a scheduled time for operating on the patient.

Example Implementation 56: The at least one non-transitory computer readable medium of any of example implementations 51 to 55, wherein the instructions cause the one or more processors to:
establish the session between the surgeon console and the patient-side robotic surgery system further in response to verifying login credentials of the surgeon.

Example Implementation 57: The at least one non-transitory computer readable medium of any of example implementations 51 to 56, wherein verifying that the at least one network connection between the surgeon console and the patient-side robotic surgery system satisfies the at least one network condition criterion comprises:
verifying that latency of the at least one network connection satisfies a latency threshold;
verifying that jitter over the at least one network connection satisfies a jitter threshold;
verifying that packet loss of the at least one network connection satisfies a packet loss threshold; and
verifying that bandwidth of the at least one network connection satisfies a bandwidth threshold.

Example Implementation 58: The at least one non-transitory computer readable medium of any of example implementations 51 to 57, wherein verifying that the at least one network connection between the surgeon console and the patient-side robotic surgery system satisfies the at least one network condition criterion comprises:

verifying that the at least one network connection comprises at least two network connections between the surgeon console and the patient-side robotic surgery system.

Example Implementation 59: At least one non-transitory computer readable medium storing instructions that, when executed by one or more processors, cause the one or more processors to:

receive a request to establish a session between a surgeon console collocated with a surgeon and a patient-side robotic surgery system collocated with a patient to allow the surgeon to remotely control movement and actuation of at least one surgical instrument and at least one imaging system of the patient-side robotic surgery system and operate on the patient; and establish the session between the surgeon console and the patient-side robotic surgery system by:

establishing a connection between a surgeon-side computing device and an audio-visual system located in an operating room where the patient-side robotic surgery system and the patient are located, the audio-visual system being configured to facilitate a two-way communication between the surgeon and one or more medical personnel in the operating room;

in response to establishing the connection between the surgeon-side computing device and the audio-visual system, causing transmission of control data from the surgeon console to the patient-side robotic surgery system for controlling movement and actuation of a surgical instrument of the patient-side robotic surgery system; and in response to failing to establish the connection between the surgeon-side computing device and the audio-visual system, disallowing transmission of control data from the surgeon console to the patient-side robotic surgery system for controlling movement and actuation of a surgical instrument of the patient-side robotic surgery system.

Example Implementation 60: The at least one non-transitory computer readable medium of example implementation 59, wherein the instructions cause the one or more processors to:

cause transmission of control data from the surgeon console to the patient-side robotic surgery system for controlling movement and actuation of a surgical instrument of the patient-side robotic surgery system in response to 1) establishing the connection between the surgeon-side computing device and the audio-visual system and 2) causing transmission of image data from an imaging system of the patient-side robotic surgery system to the surgeon console.

Example Implementation 61: The at least one non-transitory computer readable medium of example implementation 60, wherein the instructions cause the one or more processors to:

simultaneously establish the connection between the surgeon-side computing device and the audio-visual system and cause transmission of image data from the imaging system of the patient-side robotic surgery system to the surgeon console.

Example Implementation 62: The at least one non-transitory computer readable medium of any of example implementations 60 to 61, wherein the instructions cause the one or more processors to:

simultaneously cause transmission of 1) image data from the imaging system of the patient-side robotic surgery system to the surgeon console and 2) control data from the surgeon console to the patient-side robotic surgery system for controlling movement and actuation of a surgical instrument of the patient-side robotic surgery system.

Other Variations

While displaying has been used to describe certain examples of outputting information, any type of visual, auditory, or tactile output can be performed in addition to or alternatively.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value.

Features, materials, characteristics, or groups described in conjunction with a particular aspect, implementation, or example are to be understood to be applicable to any other aspect, implementation, or example described herein unless incompatible therewith. All of the features disclosed in this specification (including any accompanying claims, abstract and drawings), and/or all of the steps of any method or process so disclosed, can be combined in any combination, except combinations where at least some of such features and/or steps are mutually exclusive. The protection is not restricted to the details of any foregoing implementations. The protection extends to any novel one, or any novel combination, of the features disclosed in this specification (including any accompanying claims, abstract and drawings), or to any novel one, or any novel combination, of the steps of any method or process so disclosed.

While certain implementations have been described, these implementations have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some cases, the actual steps taken in the processes illustrated and/or disclosed may differ from those shown in the figures. Depending on the implementation, certain of the steps described above may be removed, others may be added. For example, the actual steps and/or order of steps taken in the disclosed processes may differ from those shown in the figure. Various components illustrated in the figures or described herein may be implemented as software and/or firmware on a processor, controller, ASIC, FPGA, and/or dedicated hardware. The software or firmware can include instructions stored in a non-transitory computer-readable memory. The instructions can be executed by a processor, controller, ASIC, FPGA, or dedicated hardware. Hardware components, such as controllers, processors, ASICs, FPGAs, and the like, can include logic circuitry. Furthermore, the features and attributes of the specific examples disclosed above may be combined in different ways to form additional implementations, all of which fall within the scope of the present disclosure.

Conditional language used herein, such as, among others, "can," "could", "might," "may," "e.g.," and the like, unless specifically stated otherwise, or otherwise understood within the context as used, is generally intended to convey that certain implementation include, while other implementations do not include, certain features, elements and/or states. Thus, such conditional language is not generally intended to imply that features, elements and/or states are in any way required for one or more implementations or that one or more implementations necessarily include logic for deciding, with or without author input or prompting, whether these features, elements and/or states are included or are to be performed in any particular implementation. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language, such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain implementations require at least one of X, at least one of Y and at least one of Z to each be present.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, or within less than 0.01% of the stated value.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations.

While specific implementations have been described and illustrated, such implementations should be considered illustrative only and not as limiting. Accordingly, the scope of the present disclosure is not intended to be limited by the specific disclosures of preferred implementations herein, and may be defined by claims as presented herein or as presented in the future.

What is claimed is:

1. A system for remotely controlling robotic surgery, the system comprising:
   a plurality of surgeon-side adapters configured to be integrated with a plurality of surgeon consoles, each surgeon console being configured to control at least one surgical instrument and at least one imaging system of a patient-side robotic surgery system of a plurality of patient-side robotic surgery systems, the patient-side robotic surgery system being located remotely from the surgeon console and a surgeon-side adapter integrated with the surgeon console;
   a plurality of patient-side adapters each configured to be integrated with a respective patient-side robotic surgery system; and
   at least one non-transitory computer readable medium storing instructions that, when executed by one or more processors, cause the one or more processors to:
      receive a request to establish a session between a surgeon console of the plurality of surgeon consoles and a patient-side robotic surgery system of the plurality of patient-side robotic surgery systems to allow a surgeon with whom the surgeon console is collocated to remotely control movement and actuation of at least one surgical instrument and at least one imaging system of the patient-side robotic surgery system and operate on a patient collocated with the patient-side robotic surgery system; and
      establish the session between a surgeon-side adapter of the plurality of surgeon-side adapters, the surgeon-side adapter being integrated with the surgeon console, and a patient-side adapter of the plurality of patient-side adapters, the patient-side adapter being integrated with the patient-side robotic surgery system, in response to:
         verifying that a connection has been established between a surgeon-side computing device and an audio-visual system located in an operating room where the patient-side robotic surgery system and the patient are located, the audio-visual system being configured to facilitate a two-way communication between the surgeon and one or more medical personnel in the operating room;
         verifying that the surgeon console is compatible with the patient-side robotic surgery system; and
         verifying that at least one network connection between the surgeon-side adapter and the patient-side adapter satisfies at least one network condition criterion.

2. The system of claim 1, wherein the instructions cause the one or more processors to:
   establish the session between the surgeon console and the patient-side robotic surgery system further in response to verifying that coordination has been completed between the surgeon and the one or more medical personnel in the operating room.

3. The system of claim 2, wherein coordination comprises confirming that: the surgeon is ready to operate on the patient, the patient has been prepared for being operated on, and the patient-side robotic surgery system has been prepared for operating on the patient.

4. The system of claim 1, wherein the instructions cause the one or more processors to:
   establish the session between the surgeon console and the patient-side robotic surgery system further in response to verifying that the request has been received within a time window for operating on the patient.

5. The system of claim 4, wherein the time window corresponds to a scheduled time for operating on the patient.

6. The system of claim 1, wherein the instructions cause the one or more processors to:
establish the session between the surgeon console and the patient-side robotic surgery system further in response to verifying login credentials of the surgeon.

7. The system of claim 1, wherein verifying that the at least one network connection between the surgeon-side adapter and the patient-side adapter satisfies the at least one network condition criterion comprises:
verifying that latency of the at least one network connection satisfies a latency threshold;
verifying that jitter over the at least one network connection satisfies a jitter threshold;
verifying that packet loss of the at least one network connection satisfies a packet loss threshold; and
verifying that bandwidth of the at least one network connection satisfies a bandwidth threshold.

8. The system of claim 1, wherein verifying that the at least one network connection between the surgeon-side adapter and the patient-side adapter satisfies at least one network condition criterion comprises:
verifying that the at least one network connection comprises at least two network connections between the surgeon-side adapter and the patient-side adapter.

9. At least one non-transitory computer readable medium storing instructions that, when executed by one or more processors, cause the one or more processors to:
receive a request to establish a session between a surgeon console collocated with a surgeon and a patient-side robotic surgery system collocated with a patient to allow the surgeon to remotely control movement and actuation of at least one surgical instrument and at least one imaging system of the patient-side robotic surgery system and operate on the patient collocated; and
establish the session between the surgeon console and the patient-side robotic surgery system in response to:
verifying that a connection has been established between a surgeon-side computing device and an audio-visual system located in an operating room where the patient-side robotic surgery system and the patient are located, the audio-visual system being configured to facilitate a two-way video communication between the surgeon and one or more medical personnel in the operating room;
verifying that the surgeon console is compatible with the patient-side robotic surgery system; and
verifying that at least one network connection between the surgeon console and the patient-side robotic surgery system satisfies at least one network condition criterion.

10. The at least one non-transitory computer readable medium of claim 9, wherein the instructions cause the one or more processors to:
establish the session between the surgeon console and the patient-side robotic surgery system further in response to verifying that coordination has been completed between the surgeon and the one or more medical personnel in the operating room.

11. The at least one non-transitory computer readable medium of claim 10, wherein coordination comprises confirming that: the surgeon is ready to operate on the patient, the patient has been prepared for being operated on, and the patient-side robotic surgery system has been prepared for operating on the patient.

12. The at least one non-transitory computer readable medium of claim 9, wherein the instructions cause the one or more processors to:
establish the session between the surgeon console and the patient-side robotic surgery system further in response to verifying that the request has been received within a time window for operating on the patient.

13. The at least one non-transitory computer readable medium of claim 12, wherein the time window corresponds to a scheduled time for operating on the patient.

14. The at least one non-transitory computer readable medium of claim 9, wherein the instructions cause the one or more processors to:
establish the session between the surgeon console and the patient-side robotic surgery system further in response to verifying login credentials of the surgeon.

15. The at least one non-transitory computer readable medium of claim 9, wherein verifying that the at least one network connection between the surgeon console and the patient-side robotic surgery system satisfies the at least one network condition criterion comprises:
verifying that latency of the at least one network connection satisfies a latency threshold;
verifying that jitter over the at least one network connection satisfies a jitter threshold;
verifying that packet loss of the at least one network connection satisfies a packet loss threshold; and
verifying that bandwidth of the at least one network connection satisfies a bandwidth threshold.

16. The at least one non-transitory computer readable medium of claim 9, wherein verifying that the at least one network connection between the surgeon console and the patient-side robotic surgery system satisfies the at least one network condition criterion comprises:
verifying that the at least one network connection comprises at least two network connections between the surgeon console and the patient-side robotic surgery system.

17. At least one non-transitory computer readable medium storing instructions that, when executed by one or more processors, cause the one or more processors to:
receive a request to establish a session between a surgeon console collocated with a surgeon and a patient-side robotic surgery system collocated with a patient to allow the surgeon to remotely control movement and actuation of at least one surgical instrument and at least one imaging system of the patient-side robotic surgery system and operate on the patient; and
establish the session between the surgeon console and the patient-side robotic surgery system by:
establishing a connection between a surgeon-side computing device and an audio-visual system located in an operating room where the patient-side robotic surgery system and the patient are located, the audio-visual system being configured to facilitate a two-way communication between the surgeon and one or more medical personnel in the operating room;
in response to establishing the connection between the surgeon-side computing device and the audio-visual system, causing transmission of control data from the surgeon console to the patient-side robotic surgery system for controlling movement and actuation of a surgical instrument of the patient-side robotic surgery system; and
in response to failing to establish the connection between the surgeon-side computing device and the audio-visual system, disallowing transmission of control data from the surgeon console to the patient-side robotic surgery system for controlling movement and actuation of a surgical instrument of the patient-side robotic surgery system.

18. The at least one non-transitory computer readable medium of claim 17, wherein the instructions cause the one or more processors to:
cause transmission of control data from the surgeon console to the patient-side robotic surgery system for controlling movement and actuation of a surgical instrument of the patient-side robotic surgery system in response to 1) establishing the connection between the surgeon-side computing device and the audio-visual system and 2) causing transmission of image data from an imaging system of the patient-side robotic surgery system to the surgeon console.

19. The at least one non-transitory computer readable medium of claim 18, wherein the instructions cause the one or more processors to:
simultaneously establish the connection between the surgeon-side computing device and the audio-visual system and cause transmission of image data from the imaging system of the patient-side robotic surgery system to the surgeon console.

20. The at least one non-transitory computer readable medium of claim 18, wherein the instructions cause the one or more processors to:
simultaneously cause transmission of 1) image data from the imaging system of the patient-side robotic surgery system to the surgeon console and 2) control data from the surgeon console to the patient-side robotic surgery system for controlling movement and actuation of a surgical instrument of the patient-side robotic surgery system.

* * * * *